US007196198B2

(12) United States Patent
Tani et al.

(10) Patent No.: US 7,196,198 B2
(45) Date of Patent: Mar. 27, 2007

(54) BENZOIC ACID DERIVATIVES, PROCESSES FOR THE PREPARATION THEREOF AND PHARMACEUTICAL AGENTS COMPRISING THE SAME AS ACTIVE INGREDIENT

(75) Inventors: Kousuke Tani, Mishima-gun (JP); Kaoru Kobayashi, Mishima-gun (JP); Takayuki Maruyama, Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 210 days.

(21) Appl. No.: 10/737,901

(22) Filed: Dec. 18, 2003

(65) Prior Publication Data

US 2004/0127487 A1   Jul. 1, 2004

Related U.S. Application Data

(62) Division of application No. 10/204,049, filed as application No. PCT/JP01/01263 on Feb. 21, 2001, now Pat. No. 6,710,205.

(30) Foreign Application Priority Data

Feb. 22, 2000  (JP)  ............. P. 2000-44424

(51) Int. Cl.
*C07D 211/72* (2006.01)
*C07D 211/84* (2006.01)
(52) U.S. Cl. .............. 546/293; 546/297; 546/312
(58) Field of Classification Search ............ 514/351, 514/352, 353; 546/293, 297, 312
See application file for complete search history.

(56) References Cited

U.S. PATENT DOCUMENTS 5,447,957 A   9/1995  Adams et al.

FOREIGN PATENT DOCUMENTS

GB   1 500 839   2/1978

WO   WO 95/33458   12/1995

OTHER PUBLICATIONS

Miyaura, J of Biological Chemistry, vol. 275, No. 26, Jun. 2000, pp. 19819-19828.*
Fedyk, Porc Natl Acad Sci USA, vol. 93, pp. 10978-10983, Oct. 1996.*
Bazan, Prostagladins & Other Lipid Mediators, 68-69, 2002, pp. 197-210.*
Cazin, CA 112:191376, Abstract of FFarmaco, vol. 44 (7-8), pp. 683-694 (1989).

* cited by examiner

Primary Examiner—D. Margaret Seaman
(74) Attorney, Agent, or Firm—Sughrue Miion, PLLC

(57) ABSTRACT

An agent comprising the benzoic acid of formula (I)

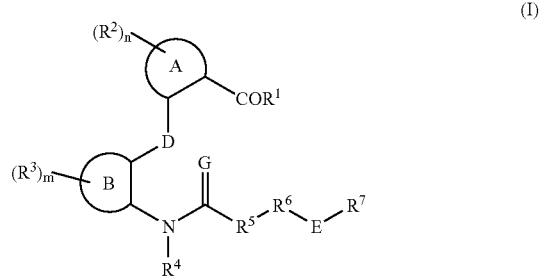

wherein A, B, $R^6$, $R^7$ are carbocyclic ring, heterocyclic ring, etc.; $R^1$ is hydroxy etc.; $R^2$, $R^3$, $R^4$ are alkyl etc.; $R^5$, D, E are alkylene, etc.; G is oxygen etc., as active ingredient.

The compound of formula (I) is considered to be useful for the treatment and/or prophylaxis of bone diseases, cancer, systemic granuloma, immunological diseases, allergy, atopy, asthma, gumboil, gingivitis, periodontitis, neurocyte death, Alzheimer's diseases, lungs injury, pulmopathy, acute hepatitis, nephritis, myocardial ischemia, Kawasaki disease, ambustion, ulcerative colitis, Crohn's disease, multiple organ failure, sleeping disorder, platelet aggregation, etc.

3 Claims, No Drawings

BENZOIC ACID DERIVATIVES, PROCESSES FOR THE PREPARATION THEREOF AND PHARMACEUTICAL AGENTS COMPRISING THE SAME AS ACTIVE INGREDIENT

This is a Divisional of U.S. application Ser. No. 10/204,049, filed Aug. 16, 2002, now U.S. Pat. No. 6,710,205; which in turn is a 371 of PCT/JP01/01263, filed Feb. 21, 2001, the disclosure of each of which is incorporated herein by reference.

TECHNICAL FIELD

The present invention relates to benzoic acid derivatives. More specifically, the present invention relates to a benzoic acid derivative of formula (I)

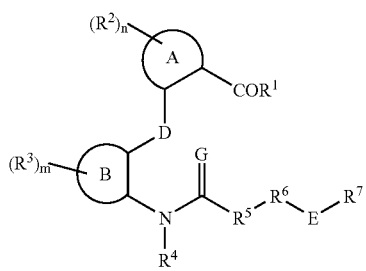

wherein all symbols have the same meanings as hereafter described, a process for the preparation thereof and a pharmaceutical agent comprising the same as active ingredient.

BACKGROUND

Prostaglandin $E_2$ (abbreviated as $PGE_2$) has been known as a metabolite in the arachidonic acid cascade. It has been known that $PGE_2$ possesses cyto-protective activity, uterine contractile activity, a pain-inducing effect, a promoting effect on digestive peristalsis, an awaking effect, a suppressive effect on gastric acid secretion, hypotensive activity, and diuretic activity.

In the recent study, it was found hat $PGE_2$ receptor was divided into some subtypes which possesses different physical roles from each other. At present, four receptor subtypes are known and they are called $EP_1$, $EP_2$, $EP_3$ and $EP_4$ (Negishi M. et al, J. Lipid Mediators Cell Signaling 12, 379–391 (1995)) respectively.

Among these subtypes, EP4 receptor was believed to be involved in suppression of TNF-α production and induction of IL-10 production. So the compounds which can bind to $EP_4$ receptor strongly and show the antagonizing activity, are useful for the prevention and/or treatment of diseases including bone diseases (such as osteoporosis, rheumatoid arthritis, osteoarthritis, abnormal bone formation etc.) and cancer (formation, proliferation, metastasis to organs, and to bones, hypercalcemia etc. and systemic granuloma, immunological diseases such as ALS, multiple sclerosis, Sjoegren's syndrome, systemic lupus erythematosus, AIDS etc. and allergy (conjunctivitis, rhinitis, contact dermatitis, psoriasis), atopic dermatitis, asthma, pyorrhea, gingivitis, periodontitis, neuronal cell death, Alzheimer's disease, pulmonary injury, hepatopathy, acute hepatopathy, nephritis, renal failure, myocardiac ischemia, Kawasaki disease, scald, ulcerative colitis, Crohn's disease, multiple organ failure etc. Moreover, EP4 is thought to be involved in sleeping disorders and platelet aggregation, so the compounds are considered to be useful.

On the other hand, in the specification of JP-A-51-115456, as a compound analogous to the compound of the present invention, 2-[2-(benzoylamino)phenylmethyl]benzoic acid is disclosed as a synthetic example. This application is only to disclose the process for the synthesis and nothing is described about pharmacological effect etc.

DISCLOSURE OF THE INVENTION

The present inventors have energetically studied to find the compound which bind to EP4 receptor specifically and show an inhibitory activity against it, to find out that the benzoic acid derivatives of formula (I) achieve the purpose and completed the present invention.

The present invention relates to (1) a benzoic acid derivative of formula (I)

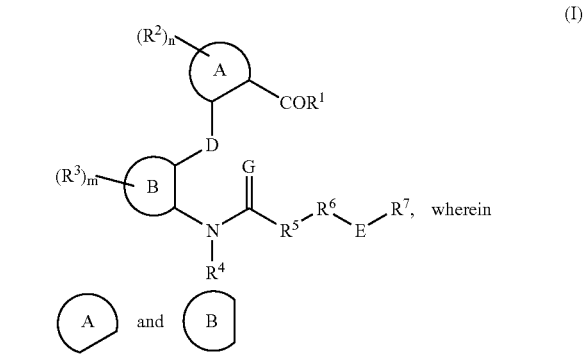

are each independently, C3~7 carbocyclic ring or 5~7 membered heterocyclic ring containing nitrogen, sulfur and/or oxygen atom, D is C1–4 alkylene, oxygen or sulfur atom, G is oxygen or sulfur, E is a bond, oxygen, sulfur, C1–4 alkylene, C1–4 alkyloxy or C1–4 oxyalkyl, $R^1$ is hydroxy, —$OR^9$ or —$NR^{10}R^{11}$, wherein $R^9$ is C1–6 alkyl, and $R^{10}$ and $R^{11}$ are each independently, hydrogen atom or C1–6 alkyl, $R^2$ and $R^3$ are each independently, C1–4 alkyl, C1–4 alkoxy, halogen atom, trihalomethyl, cyano or nitro, $R^4$ is hydrogen or C1–6 alkyl, $R^5$ is a bond, C1–6 alkylene, C1–6 alkylene substituted with C1–4 alkoxy, or C3–5 cycloalkylene, $R^6$ is C5~15 carbocyclic ring or 5~15 membered heterocyclic ring containing nitrogen, sulfur and/or oxygen, $R^7$ is hydrogen, C1–8 alkyl, C5~7 carbocyclic ring or 5~15 membered heterocyclic ring containing nitrogen, sulfur and/or oxygen, m and n are each independently, 0, 1, 2 or 3.

The rings represented by $R^6$ and $R^7$ may be substituted with C1–4 alkyl, C1–4 alkoxy, halogen, trihalomethyl, nitro, cyano or oxo, with proviso that 2-[2-(benzoylamino)phenylmethyl]benzoic acid is excluded, or a non-toxic salt thereof, (2) a process for the preparation thereof and
(3) a pharmaceutical agent comprising the same as active ingredient.

DETAILED DESCRIPTION OF THE INVENTION

In the formula (I), C1–6 alkyl which $R^3$, $R^9$, $R^4$, $R^{10}$, $R^{11}$ represent includes, methyl, ethyl, propyl, butyl, pentyl, hexyl and isomers thereof.

In the formula (I), alkyl in C1–4 alkoxy and alkyl which $R^2$, $R^3$, $R^5$, E, $R^6$, $R^7$ represent includes, methyl, ethyl, propyl, butyl and isomers thereof.

In the formula (I), C1–8 alkyl which $R^7$ represents includes, methyl, ethyl, propyl, butyl, pentyl, hexyl, heptyl, octyl and isomers thereof.

In the formula (I), C1–4 alkylene which D and E represent include, methylene, ethylene, trimethylene, tetramethylene and isomers thereof.

In the formula (I), C1–6 alkylene which $R^5$ represents include methylene, ethylene, trimethylene, tetramethylene, pentamethylene, hexamethylene and isomers thereof.

In the formula (I), halogen atom which $R^2$, $R^3$, $R^6$, $R^7$ represent include fluorine, chlorine, bromine and iodine.

In the formula (I), C3~5 cycloalkylene which $R^5$ represents include cyclopropylene, cyclobutylene, cyclopentylene.

In the formula (I), C3~7 carbocyclic ring which A and B represent may be unsaturated or saturated, and for example the ones shown by the following formulae are included.

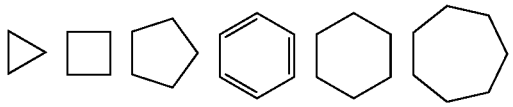

In the formula (I), 5–7 membered heterocyclic ring containing nitrogen, sulfur and/or oxygen atom which A and B represent may be saturated or unsaturated, and for example the following ones shown by the following formulae are included.

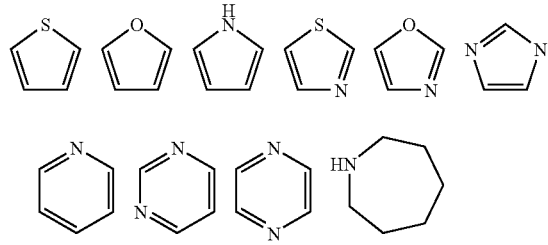

In the formula (I), C5~15 carbocyclic ring which $R^6$ and $R^7$ represent may be saturated or unsaturated and for example, the ones shown by the following formulae are included.

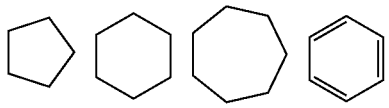

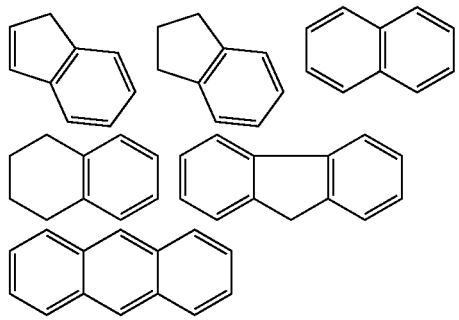

In the formula (I), 5~15 membered heterocyclic ring containing nitrogen, sulfur and/or oxygen atom which $R^6$ and $R^7$ represent may be saturated or unsaturated, and for example, the ones shown by the following formulae are included.

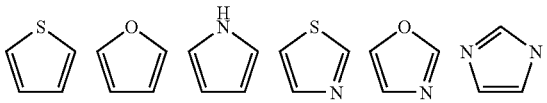

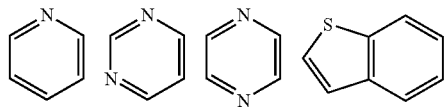

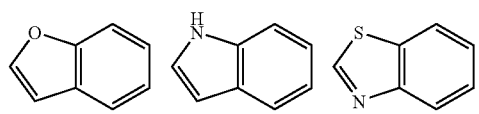

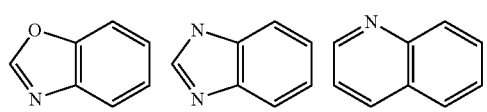

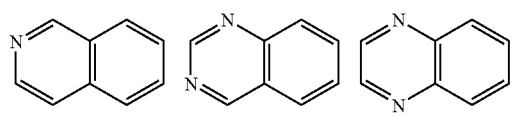

Unless otherwise specified, all isomers are included in the present invention. For example, alkyl, alkenyl and alkynyl groups include straight-chain and also branched-chain ones. In addition, isomers in double bond, ring, fused ring (E-, Z-, cis-, trans-isomer), isomers generated from asymmetric carbon atom(s) (R-, S-, α-, β-isomer, enantiomer, diastereomer), optically active isomers having optical rotation (D-, L-, d-, l-isomer), polar compounds separated by chromatography (more polar compound, less polar compound), equilibrium compounds, mixtures thereof at arbitrary ratios and racemic mixtures are included in branched-chain alkyl are included in the present invention.

In the compounds of the present invention of formula (I), the compounds described in examples and the compounds shown in the following tables 1~3 and corresponding esters and amides thereof are preferable.

TABLE 1
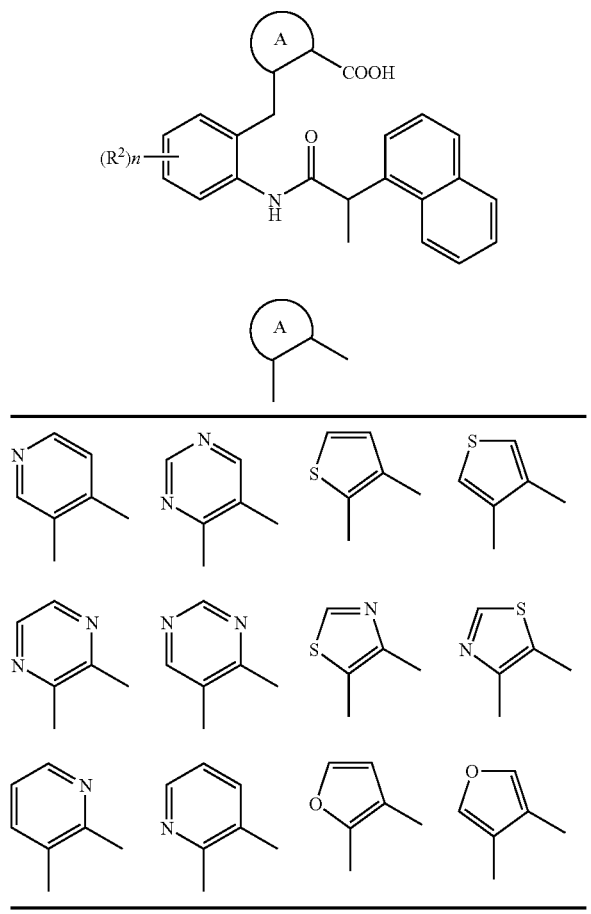
TABLE 2
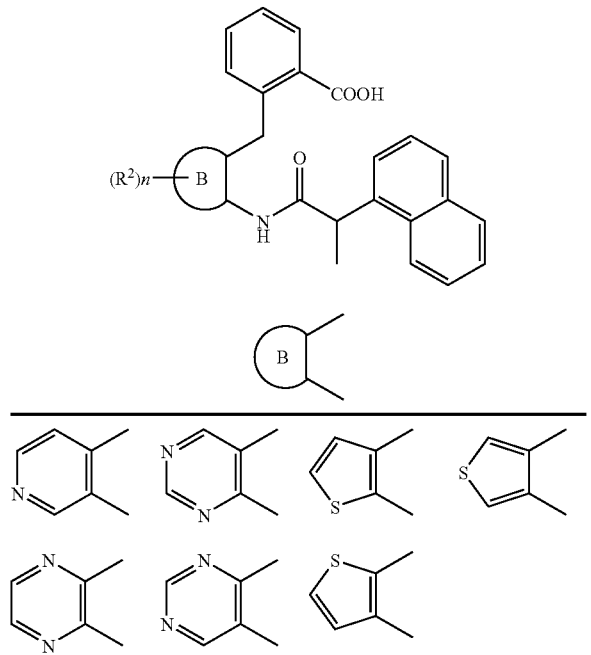
TABLE 2-continued
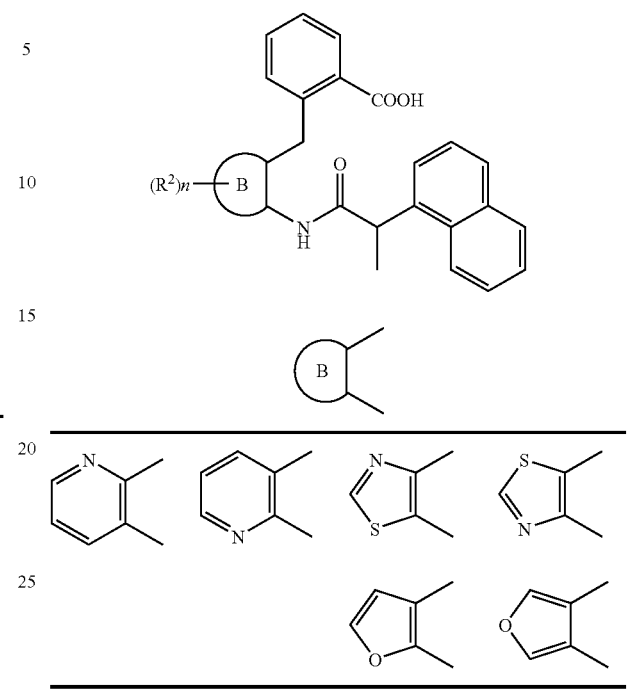
TABLE 3
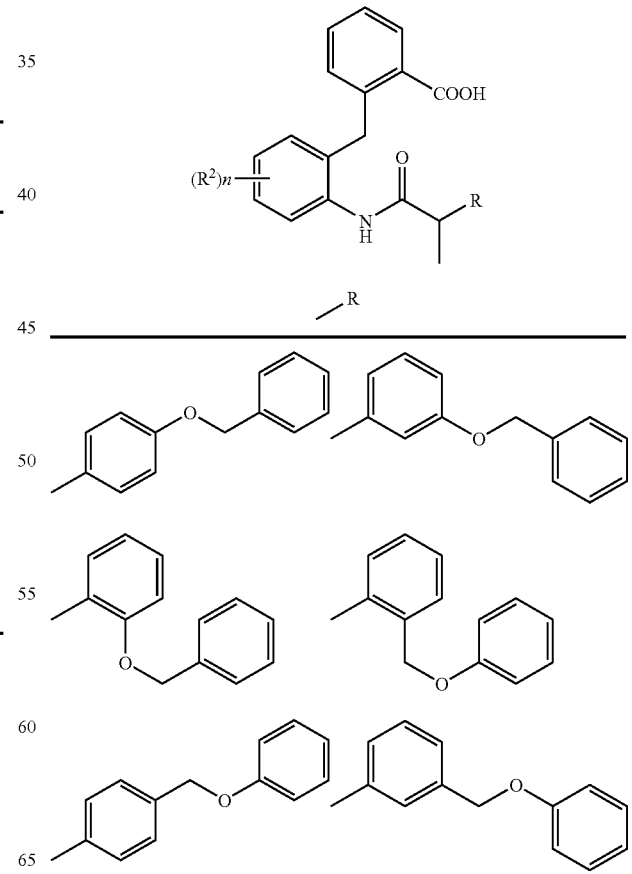

TABLE 3-continued

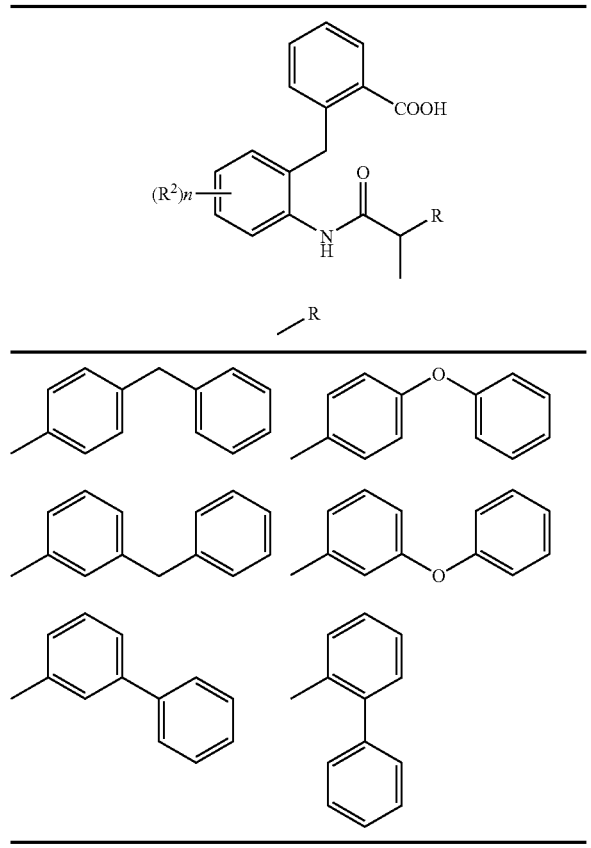

[Salt]

The compound of the present invention of formula (I) may be converted into a corresponding salt by known methods. Non-toxic and water-soluble salts are preferable. Appropriate salts are, salts of alkali metals (potassium, sodium, etc.), salts of alkaline-earthmetals, ammonium salts, pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.). The compound of the present invention of formula (I) and a salt thereof may also be converted into hydrates by known methods.

[Processes for the Preparation of the Compound of the Present Invention]

(a) Among the compound of formula (I), the compound wherein $R^1$ is hydroxy, i.e. the compound of formula (Ia)

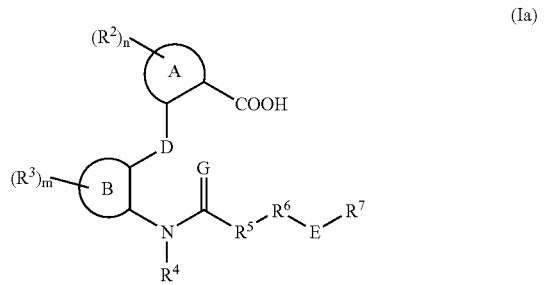

(Ia)

wherein all symbols have the same meaning as above, may be prepared by subjecting to hydrolysis under alkaline conditions the compound of formula (Ib)

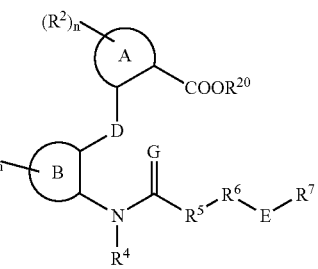

(Ib)

wherein $R^{20}$ is C1–6 alkyl and the other symbols have the same meaning as above.

Hydrolysis under alkaline conditions is known, for example, it is carried out in a water-miscible organic solvent (e.g. ethanol, tetrahydrofuran (THF), dioxane, etc.) using an aqueous solution of alkali (e.g. sodium hydroxide, potassium hydroxide, potassium carbonate, etc.) at a temperature of −10~90° C.

(b) Among the compound of formula (I), the compound wherein $R^1$ is —$NR^{10}OR^{11}$, wherein all symbols have the same meaning as above, i.e. the compound of formula (Ic)

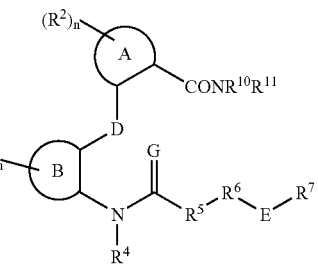

(Ic)

wherein all symbols have the same meanings as above, may be prepared by subjecting to amidation reaction the compound of formula (Ia) and the compound of formula $$HNR^{10}R^{11} \qquad (II)$$

wherein all symbols have the same meaning as above.

Amidation reaction is known, for example, it is carried out in an inert organic solvent (e.g. THF, methylene chloride, benzene, acetone, acetonitrile or a mixture thereof) in the presence or absence of a tertiary amines (dimethylaminopyridine, pyridine, triethylamine, etc.), using a condensing agent (1,3-dicyclohexylcarbodiimide(DCC), 1-ethyl-3-[3-(dimethylamino)propyl]carbodiimide(EDC), etc.) or acid halide (oxalyl chloride, thionyl chloride, phosphorus oxychloride, etc.) at a temperature of 0~50° C.

(c) The compound of formula (Ib) may be prepared by subjecting to amidation reaction the compound of formula (III)

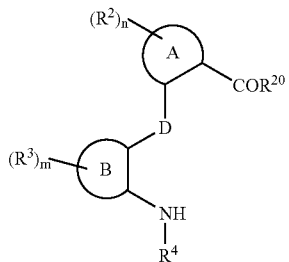

(III)

wherein all symbols have the same meaning as above, and the compound of formula (IV)

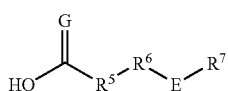 (IV)

wherein all symbols have the same meaning as above. Amidation reaction may be carried out by the same method as above described.

The compound of formula (III) maybe prepared according to the following reaction schemes (A), (B) and (C). The compound of formula (IV) may be known per se or may be prepared by known methods.

The symbols in each reaction scheme represent the followings or the same meaning as above.

$X^1$, $X^2$, $X^3$: halogen atom;
$D^1$: C1~4 alkylene;
$D^2$: oxygen or sulfur atom

Reaction Scheme (A)

when D is alkylene:

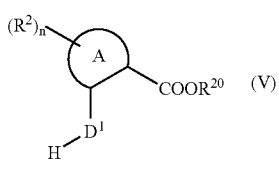 (V)

↓ halogenation

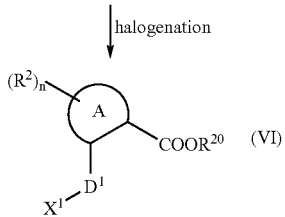 (VI)

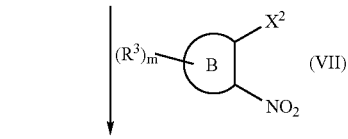 (VII)

↓

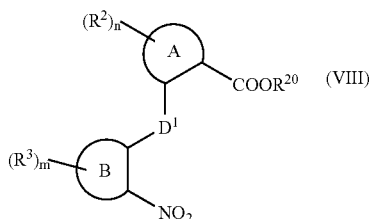 (VIII)

1) Reduction
2) $R^4\text{—}X^3$

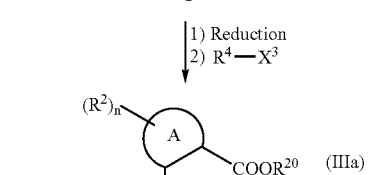 (IIIa)

Reaction Scheme (B)

when D is alkylene:

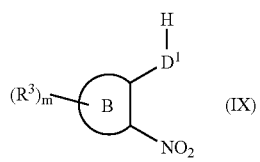 (IX)

↓ halogenation

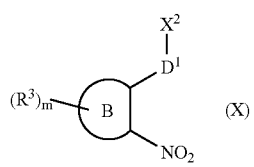 (X)

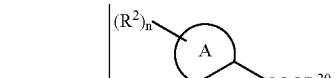

↓

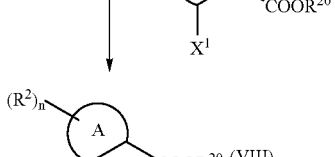 (VIII)

1) Reduction
2) $R^4\text{—}X^3$

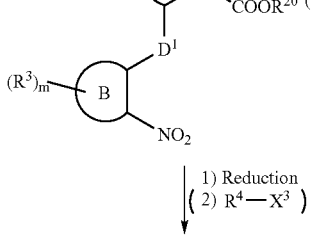 (IIIa)

Reaction Scheme (C)

when D is oxygen or sulfur:

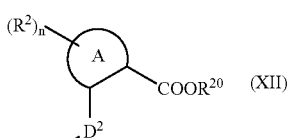 (XII)

↓

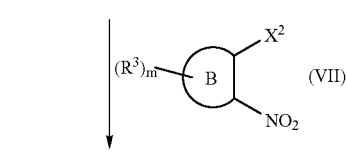 (VII)

↓

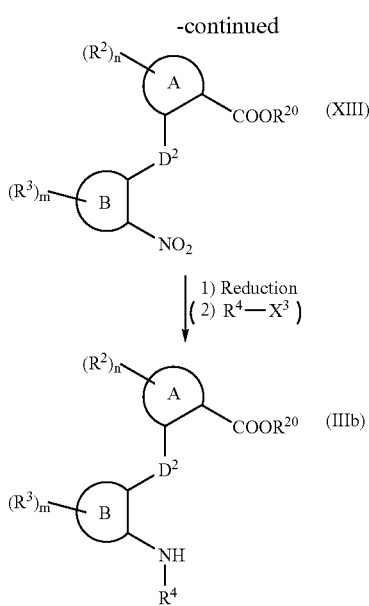

[Starting Materials and Reagents]

Each reaction in the above reaction schemes may be carried out by known methods. In the above reaction schemes, the compounds of formula (V), (VII), (IX), (XI) and (XII) may be known per se, or may be prepared by known methods with ease. And the other starting materials and reagents may be known per se or may be prepared by known methods.

In each reaction in the present specification, reaction products may be purified by conventional purification techniques, e.g. by distillation under atmospheric or reduced pressure, by high performance liquid chromatography, by thin layer chromatography or by column chromatography using silica gel or magnesium silicate, or by washing or by recrystallization. Purification may be carried out after each reaction or after a series of reactions.

[Pharmacological Activities]

The compounds of the present invention of formula (I) bind strongly and show an antagonizing activity on the $EP_4$ subtype receptor, which is one of the $PGE_2$ receptors.

For example, in a standard laboratory test, such effects of the compound of the present invention were confirmed by binding assay using the cell expressing the prostanoid receptor subtypes.

(i) Binding Assay Using Cell Expressing The Prostanoid Receptor Subtypes

The preparation of membrane fraction was carried out according to the method of Sugimoto et al [J. Biol. Chem. 267, 6463–6466 (1992)], using CHO cell expressing prostanoid receptor subtype (mouse $EP_1$, $EP_2$, $EP_3$, $EP_4$ and human IP).

The standard assay mixture containing membrane fraction (0.5 mg/mL), [$^3$H]-$PGE_2$ in a final volume of 200 μl was incubated for 1 hour at room temperature. The reaction was terminated by addition of 3 mL of ice-cold buffer. The mixture was rapidly filtered through a glass filter (GF/B) under reduced pressure. The radioactivity associated with the filter was measured by liquid scintillation counter.

Kd and Bmax values were determined from Scatchard plots [Ann. N.Y. Acad. Sci. 51, 660(1949)]. Non-specific binding was calculated as the amount bound in the presence of an excess (2.5 μM) of unlabeled $PGE_2$. In the experiment for competition of specific [$^3$H]-$PGE_2$ binding by the compounds of the present invention, [$^3$H]-$PGE_2$ was added at a concentration of 2.5 mM and the compound of the present invention was added at various concentrations. The following buffer was used in all reactions.

Buffer: 10 mM potassium phosphate (pH 6.0), 1 mM EDTA, 10 mM $MgCl_2$, 0.1 M NaCl.

The dissociation constant (Ki) (μM) of each compound was calculated by the following equation.

$$Ki=IC_{50}/(1+([C]/Kd))$$

The results are shown in Table 4.

TABLE 4

| Example No. | $EP_4$ Ki (μM) |
|---|---|
| 2(1) | 0.0027 |
| 2(15) | 0.0065 |
| 4(1) | 0.0105 |

As mentioned above, it is clear that the compounds of the present invention can bind strongly on the $EP_4$ subtype receptor.

(ii) $EP_4$ Antagonizing Activity Assay Using the Cell Expressing the Prostanoid Receptor Subtypes The preparation of CHO cell expressing prostanoid receptor subtype was carried out according to the method of Nishigaki et al [FEBS lett., 364, 339–341(1995)]. The cells were cultured in 24-well microplates ($10^5$ cells/well) for two days before experiments. After washing each well with 500 μL of MEM (minimum essential medium), thereto was added 450 μL of assay medium (MEM containing 1 mmol/L IBMX, 1% BSA), and the mixture was incubated for 10 minutes at 37° C. Then $PGE_2$ alone or a combination with a test compound (50 μL) were added, and the mixture was incubated for 10 minutes at 37° C. And reaction was terminated by addition of ice-cold TCA (10% W/V, 500 μL). This reaction mixture was freezed once (−80° C.) and thawed, and cells were harvested using a scraper. After centrifugation (13,000 r.p.m., for 3 minutes), cAMP content was measured using cAMP assay kit. That is, the supernatant (125 μL) was diluted with 500 μL of [$^{125}$I]-cAMP assay kit buffer (Amersham), and mixed with 0.5 mol/L tri-n-octylamine/chloroform solution (1 mL) was mixed. After removal of TCA from chloroform layer, cAMP content in the aqueous layer was quantified according to the method of kit manuals.

An antagonizing activity of compound ($IC_{50}$ value) was calculated as a inhibitory rate on the condition using 100 nM $PGE_2$ as an agonist. This concentration of $PGE_2$ served a submaximal effect on cAMP production.

TABLE 5

| | $EP_4$ antagonizing activity | |
|---|---|---|
| Example No. | | $EP_4$ antagonizing activity $IC_{50}$ (μM) |
| 2(1) | | 0.01 |

As mentioned above, it is clear that the compounds of the present invention show an antagonizing activity on the $EP_4$ subtype receptor.

[Toxicity]

The toxicity of the compounds of the formula (I) of the present invention is very low and therefore, it is confirmed that these compounds are safe for use as medicine.

INDUSTRIAL APPLICABILITY

[Application to Pharmaceuticals]

The compounds of the present invention of the formula (I) can bind and show the antagonizing activity on the $PGE_2$ receptor. Particularly, they bind to $EP_4$ subtype receptor and show the antagonizing activity, so they are useful for the prevention and/or treatment of bone diseases such as osteoporosis, rheumatoid arthritis, osteoarthritis, abnormal bone formation), cancer (e.g. cancer formation, cancer proliferation, cancer metastasis to organs and to bones, hypercalcemia accompanied by cancer metastasis to bones, etc.) and systemic granuloma, immunological diseases (e.g. amyotropic lateral sclerosis (ALS), multiple sclerosis, Sjoegren's syndrome, systemic lupus erythematosus, AIDS), allergy (conjunctivitis, rhinitis, contact dermatitis, psoriasis, etc.), atopy (atopic dermatitis etc.), asthma, pyorrhea, gingivitis, periodontitis, neuronal cell death, Alzheimer's disease, pulmonary injury, hepatopathy, acute hepatopathy, nephfitis, renal failure, myocardiac ischemia, Kawasaki disease, scald, ulcerative colitis, Crohn's disease, multiple organ failure etc. Moreover, it was thought to be involved in sleeping disorder and platelet aggregation, so the usefulness of inhibitors is expected.

For the purpose described above, the compounds of formula (I), of the present invention, non-toxic salts thereof may be normally administered systemically or topically, usually by oral or parenteral administration.

The doses to be administered are determined depending upon, for example, age, body weight, symptom, the desired therapeutic effect, the route of administration, and the duration of the treatment, etc. In the human adult, the doses per person at a time are generally from 0.1 mg to 100 mg, by oral administration, up to several times per day, and from 0.01 mg to 10 mg, by parenteral administration (preferably intravenous administration), up to several times per day, or continuous administration between 1 and 24 hours per day into vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) are, admixed with at least one inert diluent such as lactose, mannitol, glucose, hydroxypropyl cellulose, microcrystalline cellulose, starch, polyvinyl pyrrolidone or magnesium metasilicate aluminate.

The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, aspartic acid. The tablets or pills may, if desired, be coated with film of gastric- or enteric-coating agents (e.g. sugar, gelatin, hydroxypropyl cellulose or hydroxypropyl cellulose phthalate), or be coated with two or more films. And further, coating may include containment within capsules of absorbable materials such as gelatin.

Liquid compositions for oral administration include pharmaceutically acceptable emulsions, solutions, syrups and elixirs. In such compositions, one or more of the active compound(s) are dissolved, suspended or emulsified in inert diluent(s) commonly used (e.g. purified water, ethanol). Furthermore, such liquid compositions may also comprise wetting agents or suspending agents, emulsifying agents, sweetening agents, flavouring agents, perfuming agents, preserving agents etc.

Other compositions for oral administration include sprays which may be prepared by known methods, which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or U.S. Pat. No. 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSORBATE80 (registered trade mark), etc.

Such compositions may comprise additional diluents: e.g. preserving agents, wetting agents, emulsifying agents, dispersing agents, stabilizing agents, assisting agents such as assistant agents for dissolving (for example, glutamic acid, aspartic acid). They may be sterilized for example, by filteration through a bacteria-retaining filter, by incorporation of sterilizing agents in the compositions or by irradiation. They may also be manufactured in the form of sterile solid compositions which can be dissolved in sterile water or some other sterile diluent for injection immediately before use.

Other compositions for parenteral administration include liquids for external use, and endemic liniments, ointments, suppositories and pessaries which comprise one or more of the active compound(s) and may be prepared by known methods.

Best Mode for Carrying Out the Invention

The following reference examples and examples illustrate the present invention, but do not limit the present invention.

The solvents in the parentheses show the eluting or developing solvents and the ratios of the solvents used are by volume in chromatographic separations or TLC.

The solvents in the parentheses in NMR show the solvents used in measurement.

REFERENCE EXAMPLE 1

1-nitro-2-iodo-4-chlorobenzene

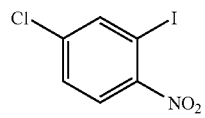

To a suspension of 2-nitro-5-chloroaniline (5.00 g) in conc. hydrochloric acid (30 ml) under cooling with ice, was added a solution of sodium nitrite (2.10 g) in water (10 ml) dropwise and the mixture was stirred for 30 minutes. Under cooling with ice, to this solution was added a solution of potassium iodide (5.30 g) in water (20 ml) dropwise and the mixture was stirred for 1 hour at room temperature. The solid that appeared was collected by filtration and was dissolved in ethyl acetate and was dried and concentrated to give a crude product of the title compound. It was purified by recrystallization from ethyl acetate-hexane to give the title compound having the following physical data (5.14 g, yellow powder).

TLC: Rf 0.69 (n-hexane:ethyl acetate=9:1); NMR (CDCl₃): δ 8.06 (d, J=2.2 Hz, 1H), 7.85 (d, J=8.6 Hz, 1H), 7.47 (dd, J=8.6, 2.2 Hz, 1H).

REFERENCE EXAMPLE 2

2-bromomethylbenzoic acid methyl ester

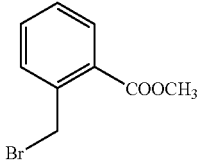

To a solution of 2-methylbenzoic acid methyl ester (33.0 g) in tetrachlorocarbon (440 ml) were added N-bromosuccinimide (43.0 g) and AIBN (2,2'-azobisisobutyronitrile, 361 mg) and the mixture was refluxed for 30 minutes. The reaction mixture was cooled down to 0° C. and cinnamoic acid that appeared were filtered off and the filtrate was concentrated. The residue was purified by distillation under reduced pressure to give the title compound having the following physical data (28.0 g, colorless oil).

TLC: Rf 0.65 (n-hexane:ethyl acetate=4:1); NMR (CDCl₃): δ 7.97 (d, J=7.4 Hz, 1H), 7.56–7.30 (m, 3H), 4.96 (s, 2H), 3.95 (s, 3H).

REFERENCE EXAMPLE 3

2-(5-chloro-2-nitrophenylmethyl)benzoic acid methyl ester

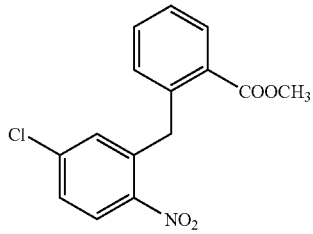

To a suspension of zinc powder (1.50 g) in THF (7.5 ml) was added dibromoethane (catalytic amount) and the mixture was stirred for five minutes at 50° C. to activate the zinc. To this suspension was added a solution of 2-bromomethylbenzoic acid methyl ester (3.50 g; prepared in reference example 2) in THF (7.5 ml) at 0° C. slowly and the mixture was stirred for 30 minutes at the temperature to give a solution of 2-carbomethoxybenzylzinc (II) in THF.

A solution of 1-nitro-2-iodo-4-chlorobenzene (1.00 g; prepared in reference example 1), bis(dibenzylideneacetone) palladium (0) (20 mg) and 1,1'-bis(diphenylphosphino)ferrocene (20 mg) in THF (10 ml) was degassed. Thereto was added 2-carbomethoxybenzyl zinc (THF solution; 6.0 ml) at room temperature and the mixture was stirred for 15 minutes at room temperature and 1 hour at 50° C. The solution was cooled down and thereto was added a saturated aqueous solution of ammonium chloride and was extracted with ethyl acetate. The organic layer was washed with water and a saturated aqueous solution of sodium chloride, dried and was concentrated. The residue was purified by column chromatography on silica gel to give the title compound (849 mg; yellow oil) having the following physical data.

TLC: Rf 0.38 (n-hexane:ethyl acetate=9:1); NMR (CDCl₃): δ 8.03 (dd, J=7.8, 1.5 Hz, 1H), 7.94 (d, J=8.7 Hz, 1H), 7.50 (m, 1H), 7.38 (m, 1H), 7.31 (dd, J=8.7, 2.1 Hz, 1H), 7.17 (m, 1H), 6.96 (d, J=2.1 Hz, 1H), 4.65 (s, 2H), 3.79 (s, 3H).

REFERENCE EXAMPLE 4

2-(2-amino-5-chlorophenylmethyl)benzoic acid methyl ester

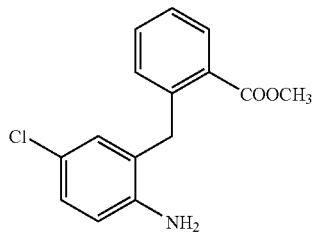

To a solution of 2-(2-nitro-5-chlorophenylmethyl) benzoic acid methyl ester (840 mg; prepared in reference example 3) in a mixture of acetic acid-water (5:1; 12 ml) was added steel powder (768 mg) and the mixture was added for 20 minutes at 80° C. The suspension was poured into ice-water and was extracted with ethyl acetate. The organic layer was washed with water, a saturated aqueous solution of sodium bicarbonate and a saturated aqueous solution of sodium chloride successively, dried, and was concentrated. The residue was purified by column chromatography on silica gel to give the title compound (363 mg) having the following physical data.

TLC: Rf 0.53 (n-hexane:ethyl acetate=2:1); NMR (CDCl₃): δ 7.91 (dd, J=7.6, 1.4 Hz, 1H), 7.43 (m, 1H), 7.30 (m, 1H), 7.17 (m, 1H), 7.02 (dd, J=8.4, 2.6 Hz, 1H), 6.92 (d, J=2.6 Hz, 1H), 6.59 (d, J=8.4 Hz, 1H), 4.20 (s, 2H), 3.89 (s, 3H), 3.80 (br, 2H).

EXAMPLE 1

2-[5-chloro-2-[2-(1-naphthyl)propanoylamino]phenylmethyl]benzoic acid methyl ester

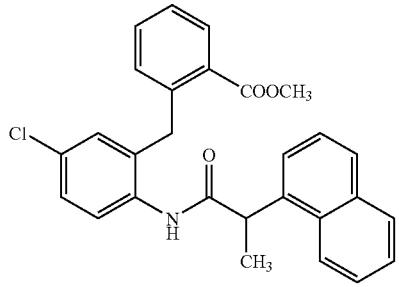

To a solution of 2-(2-amino-5-chlorophenylmethyl)benzoic acid methyl ester (339 mg; prepared in Reference Example 4) and pyridine (0.20 ml) in methylene chloride (3 ml) was added 2-(1-naphthyl)propionyl chloride (295 mg) in methylene chloride (2 ml) and the mixture was stirred for 2.5 hours at room temperature. To this solution was added a saturated aqueous solution of sodium bicarbonate and was extracted with ethyl acetate. The organic layer was washed with water and a saturated aqueous solution of sodium chloride, dried and was concentrated to give a crude product of the compound of the present invention. The residue was purified by recrystallization from ethyl acetate-hexane to give the compound of the present invention (455 mg, white powder).

TLC: Rf 0.52 (n-hexane:ethyl acetate=3:1); NMR (CDCl₃): δ 8.06–7.96 (m, 3H), 7.83 (m, 1H), 7.69 (m, 1H), 7.55–7.43 (m, 3H), 7.33–7.08 (m, 5H), 6.98 (d, J=2.2 Hz, 1H), 6.87 (dd, J=7.6, 1.0 Hz, 1H), 4.43 (q, J=7.0 Hz, 1H), 3.96 (d, J=16.0 Hz, 1H), 3.72 (d, J=16.0 Hz, 1H), 3.65 (s, 3H), 1.64 (d, J=7.0 Hz, 3H).

EXAMPLE 2

2-[5-chloro-2-[2-(1-naphthyl)propanoylamino]phenylmethyl]benzoic acid

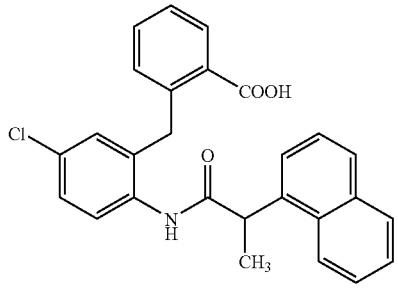

To a solution of 2-[5-chloro-2-[2-(1-naphthyl)propanoylamino]phenyl methyl]benzoic acid methyl ester (440 mg; prepared in Example 1.) in methanol-dioxane (1:1; 8 ml) was added 2 mol/L aqueous solution of sodium hydroxide (3 ml) and the mixture was stirred for 3 hours at 50° C. The solution was acidified with hydrochloric acid and was extracted with ethyl acetate. The organic layer was washed with water and a saturated aqueous solution of sodium chloride, dried and concentrated to give a crude crystal. It was washed with ethyl acetate-hexane to give the title compound (342 mg; white powder) having the following physical data.

TLC: Rf 0.39 (n-hexane:ethyl acetate=1:1); NMR (DMSO-$d_6$): δ 9.65 (s, 1H), 8.19 (m, 1H), 7.91 (m, 1H), 7.86–7.76 (m, 2H), 7.56–7.27 (m, 7H), 7.23 (dd, J=8.4, 2.4 Hz, 1H), 6.96 (d, J=6.6 Hz, 1H), 6.86 (d, J=2.4 Hz, 1H), 4.65 (q, J=6.9 Hz, 1H), 4.27 (d, J=16.5 Hz, 1H), 4.21 (d, J=16.5 Hz, 1H), 1.48 (d, J=6.9 Hz, 3H).

Example 2(1)~Example 2(30)

By the same procedure as described in Reference Example 1→Reference Example 2→Reference Example 3→Reference Example 4→Example 1→Example 2, the compounds having the following physical data were given.

Example 2(1)

2-[2-[2-(1-naphthyl)propanoylamino]phenylmethyl]benzoic acid

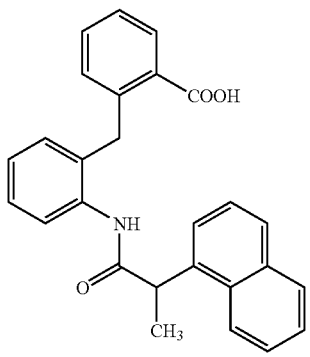

TLC: Rf 0.61 (chloroform:methanol=9:1); NMR (DMSO-$d_6$): δ 9.60 (s, 1H), 8.32–8.16 (m, 1H), 7.92–7.72 (m, 3H), 7.64–6.84 (m, 11H), 4.65 (q, J=6.8 Hz, 1H), 4.27 (s, 2H), 1.50 (d, J=6.8 Hz, 3H).

Example 2(2)

2-[2-[2-(2-naphthyl)propanoylamino]phenylmethyl]benzoic acid

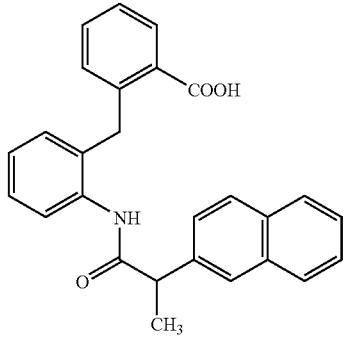

TLC: Rf 0.58 (chloroform:methanol=9:1); NMR (DMSO-$d_6$): δ 9.56(s, 1H), 7.94–7.72 (m, 5H), 7.58–7.40 (m, 4H), 7.38–6.86 (m, 6H), 4.29 (s, 2H), 4.04 (q, J=7.2 Hz, 1H), 1.45 (d, J=7.2 Hz, 3H).

Example 2(3)

2-[2-[2-(4-pentylphenyl)propanoylamino]phenylthio]benzoic acid

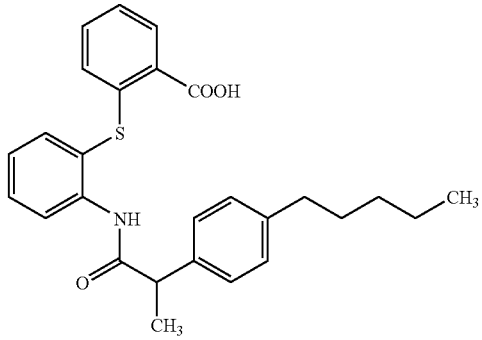

TLC: Rf 0.44 (chloroform:methanol=19:1); NMR (CDCl$_3$): δ 8.55 (dd, J=8.1, 1.2 Hz, 1H), 8.23 (bs, 1H), 8.19 (m, 1H), 7.56–7.47 (m, 2H), 7.24–7.10 (m, 3H), 6.92 (s, 4H), 6.44 (m, 1H), 3.56 (q, J=7.4 Hz, 1H), 2.49 (m, 2H), 1.59–1.19 (m, 6H), 1.44 (d, J=7.4 Hz, 3H), 0.85 (t, J=6.9 Hz, 3H).

Example 2(4)

2-[2-[2-(4-biphenyl)propanoylamino]phenylmethyl]benzoic acid

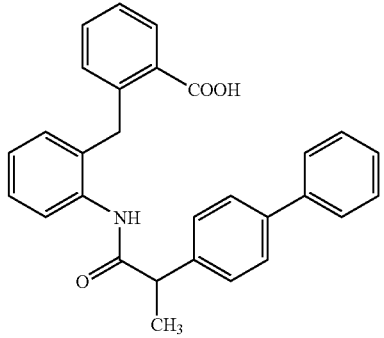

TLC: Rf 0.59 (chloroform:methanol=9:1); NMR (CDCl$_3$): δ 8.01 (d, J=8.1 Hz, 1H), 7.91 (d, J=7.5 Hz, 1H), 7.67 (bs, 1H), 7.59–6.95 (m, 15H), 4.23 (d, J=17 Hz, 1H), 4.16 (d, J=17 Hz, 1H), 3.67 (q, J=7.1 Hz, 1H), 1.50 (d, J=7.1 Hz, 3H).

Example 2(5)

2-[2-[2-(1,2,3,4-tetrahydroquinolin-1-yl)propanoylamino]phenylmethyl]benzoic acid

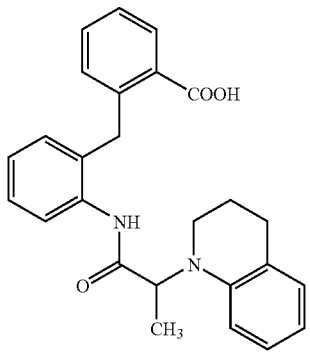

TLC: Rf 0.48 (chloroform:methanol=19:1); NMR (DMSO-d$_6$): δ 9.29 (bs, 1H), 7.81 (d, J=7.5 Hz, 1H), 7.51 (d, J=8.1 Hz, 1H), 7.42–7.25 (m, 2H), 7.19 (t, J=7.7 Hz, 1H), 7.06 (t, J=7.7 Hz, 1H), 6.97–6.84 (m, 4H), 6.63–6.47 (m, 2H), 4.46 (q, J=7.0 Hz, 1H), 4.24 (s, 2H), 3.16 (t, J=5.6 Hz, 2H), 2.62 (t, J=6.5 Hz, 2H), 1.87–1.66 (m, 2H), 1.27 (d, J=7.0 Hz, 3H).

Example 2(6)

2-[3-chloro-2-[2-(1-naphthyl)propanoylamino]phenylmethyl]benzoic acid

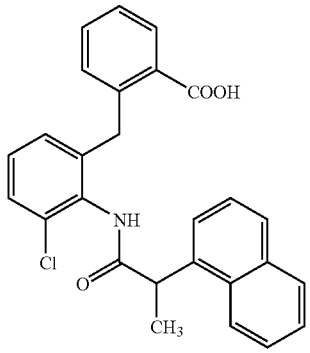

TLC: Rf 0.42 (n-hexane:ethyl acetate=1:1); NMR (DMSO-d$_6$): δ 9.85 (s, 1H), 8.30 (m, 1H), 7.90 (m, 1H), 7.85 (dd, J=7.8, 1.5 Hz, 1H), 7.79 (d, J=8.1 Hz, 1H), 7.56–7.27 (m, 7H), 7.15 (t, J=7.8 Hz, 1H), 6.94 (d, J=7.2 Hz, 1H), 6.81 (d, J=7.2 Hz, 1H), 4.68 (q, J=6.9 Hz, 1H), 4.21 (brs, 2H), 1.55 (d, J=6.9 Hz, 3H).

Example 2(7)

2-[5-methoxy-2-[2-(1-naphthyl)propanoylamino]phenylmethyl]benzoic acid

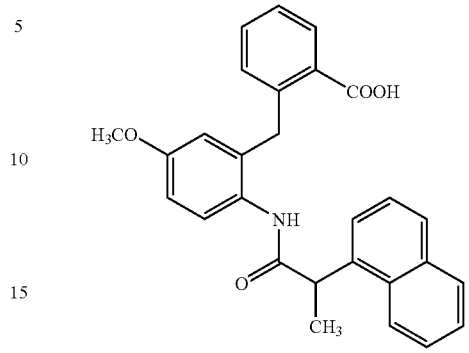

TLC: Rf 0.52 (chloroform:methanol=9:1); NMR (DMSO-d$_6$): δ 9.55 (s, 1H), 8.33 (m, 1H), 8.00 (m, 1H), 7.89 (m, 2H), 7.65–7.31 (m, 7H), 7.01 (d, J=6.9 Hz, 1H), 6.85 (dd, J=8.7, 2.7 Hz, 10H), 6.54 (d, J=2.7 Hz, 1H), 4.69 (q, J=6.9 Hz, 1H), 4.33 (d, J=16.5 Hz, 1H), 4.26 (d, J=16.5 Hz, 1H), 3.72 (s, 3H), 1.56 (d, J=6.9 Hz, 3H).

Example 2(8)

2-[2-[2-(1-naphthyl)acetylamino]phenylmethyl]benzoic acid

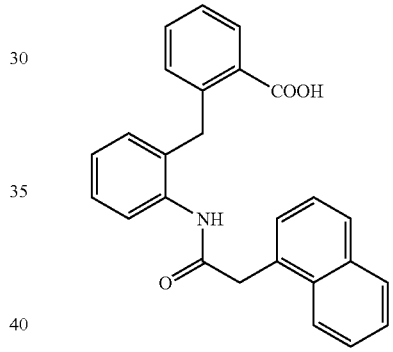

TLC: Rf 0.50 (chloroform:methanol=9:1); NMR (DMSO-d$_6$): δ 9.80 (s, 1H), 8.13 (m, 1H), 8.02–7.87 (m, 3H), 7.62–7.38 (m, 7H), 7.26 (t, J=6.9 Hz, 1H), 7.13 (m, 2H), 7.00 (m, 1H), 4.44 (s, 2H), 4.20 (s, 2H)

Example 2(9)

2-[2-[2-(1-naphthyl)carbonylamino]phenylmethyl]benzoic acid

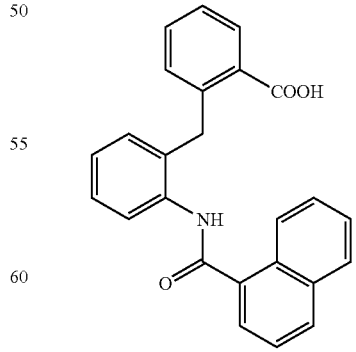

TLC: Rf 0.48 (chloroform:methanol=9:1); NMR (DMSO-d$_6$): δ 10.1 (s, 1H), 8.07–7.95 (m, 3H), 7.84 (d, J=7.5 Hz, 1H), 7.63–7.40 (m, 6H), 7.35–7.27 (m, 2H), 7.18 (t, J=7.5 Hz, 1H), 7.04 (t, J=7.5 Hz, 2H), 4.46 (s, 2H).

Example 2(10)

2-[3-methoxy-2-[2-(1-naphthyl)propanoylamino]phenylmethyl]benzoic acid

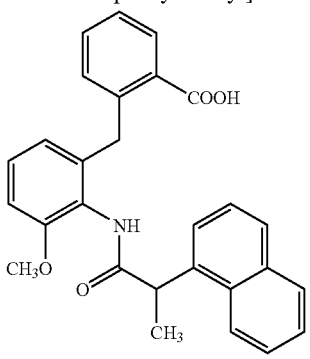

TLC: Rf 0.55 (chloroform:methanol=9:1); NMR (DMSO-d$_6$): δ 9.34 (s, 1H), 8.31 (m, 1H), 7.92–7.76 (m, 3H), 7.54–7.24 (m, 6H), 7.09 (t, J=8.1 Hz, 1H), 6.96 (d, J=8.1 Hz, 1H), 6.86 (d, J=8.1 Hz, 1H), 6.45 (d, J=8.1 Hz, 1H), 4.63 (q, J=7.2 Hz, 1H), 4.20 (d, J=15.9 Hz, 1H), 4.13 (d, J=15.9 Hz, 1H), 3.70 (s, 3H), 1.52 (d, J=7.2 Hz, 3H).

Example 2(11)

2-[4-methoxy-2-[2-(1-naphthyl)propanoylamino]phenylmethyl]benzoic acid

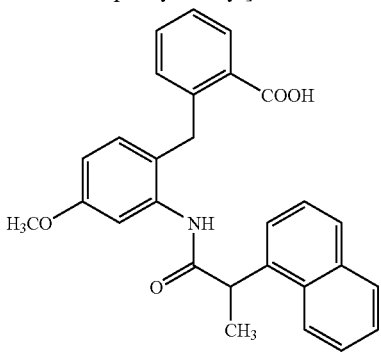

TLC: Rf 0.55 (chloroform:methanol=9:1); NMR (DMSO-d$_6$): δ 9.50 (s, 1H), 8.15 (m, 1H), 7.90 (m, 1H), 7.80–7.73 (m, 2H), 7.53–7.22 (m, 6H), 7.14 (d, J=2.4 Hz, 1H), 6.89 (dd, J=7.5, 0.9 Hz, 1H), 6.84 (d, J=8.7 Hz, 1H), 6.65 (dd, J=8.7, 2.4 Hz, 1H), 4.62 (q, J=6.9 Hz, 1H), 4.21 (d, J=17.7 Hz, 1H), 4.15 (d, J=17.7 Hz, 1H), 3.68 (s, 3H), 1.46 (d, J=6.9 Hz, 3H)

Example 2(12)

2-[4-chloro-2-[2-(1-naphthyl)propanoylamino]phenylmethyl]benzoic acid

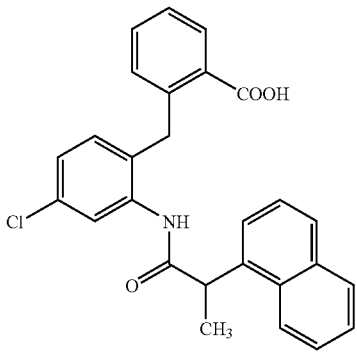

TLC: Rf 0.37 (n-hexane:ethyl acetate=1:1); NMR (DMSO-d$_6$): δ 9.70 (s, 1H), 8.16 (m, 1H), 7.92 (m, 1H), 7.82–7.77 (m, 2H), 7.60 (d, J=2.1 Hz, 1H), 7.56–7.26 (m, 6H), 7.11 (dd, J=8.4, 2.1 Hz, 1H), 6.93 (d, J=7.5 Hz, 1H), 6.87 (d, J=8.4 Hz, 1H), 4.66 (q, J=6.6 Hz, 1H), 4.27 (d, J=16.8 Hz, 1H), 4.20 (d, J=16.8 Hz, 1H), 1.48 (d, J=6.6 Hz, 3H).

Example 2(13)

2-[6-chloro-2-[2-(1-naphthyl)propanoylamino]phenylmethyl]benzoic acid

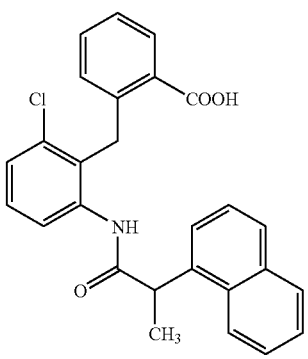

TLC: Rf 0.34 (n-hexane:ethyl acetate=1:1); NMR (DMSO-d$_6$): δ 9.77 (brs, 1H), 8.07 (d, J=8.4 Hz, 1H), 7.90–7.82 (m, 2H), 7.74 (dd, J=7.5, 1.5 Hz, 1H), 7.50–7.20 (m, 9H), 6.52 (m, 1H), 4.54 (q, J=6.9 Hz, 1H), 4.48 (brs, 2H), 1.37 (d, J=6.9 Hz, 3H).

Example 2(14)

2-[6-methoxy-2-[2-(1-naphthyl)propanoylamino]phenylmethyl]benzoic acid

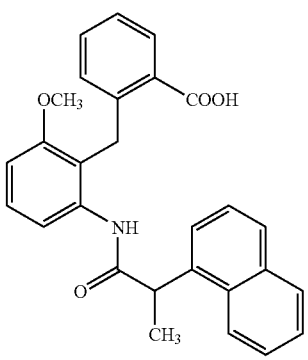

TLC: Rf 0.34 (n-hexane:ethyl acetate=1:1); NMR (DMSO-d$_6$): δ 9.54 (s, 1H), 8.10 (d, J=7.8 Hz, 1H), 7.87 (m, 1H), 7.78–7.72 (m, 2H), 7.50–7.31 (m, 4H), 7.24–7.14 (m, 3H), 7.05 (d, J=7.8 Hz, 1H), 6.83 (d, J=7.8 Hz, 1H), 6.63 (m, 1H), 4.55 (q, J=6.9 Hz, 1H), 4.28 (brs, 2H), 3.65 (s, 3H), 1.39 (d, J=6.9 Hz, 3H).

Example 2(15)

2-[4-[2-(1-naphthyl)propanoylamino]pyridin-3-ylmethyl]benzoic acid monohydrochloride

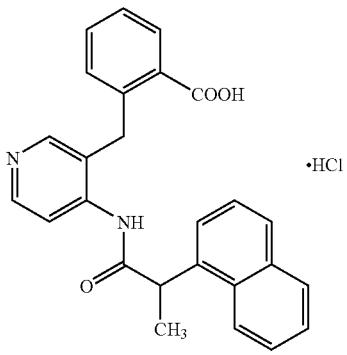

TLC: Rf 0.40 (chloroform:methanol 9:1); NMR (DMSO-$d_6$): δ 10.52 (s, 1H), 8.64 (d, J=6.6 Hz, 1H), 8.59 (d, J=6.6 Hz, 1H), 8.29 (brs, 1H), 8.04 (m, 1H), 7.94 (m, 1H), 7.82 (dd, J=7.0, 2.2 Hz, 1H), 7.72 (dd, J=7.6, 1.4 Hz, 1H), 7.56–7.48 (m, 2H), 7.46–7.30 (m, 4H), 7.12 (d, J=7.2 Hz, 1H), 4.93 (q, J=6.9 Hz, 1H), 4.47 (brs, 2H), 1.52 (d, J=6.9 Hz, 3H).

Example 2(16)

2-[2-[2-(1-naphthyl)propanoylamino]phenoxy]benzoic acid

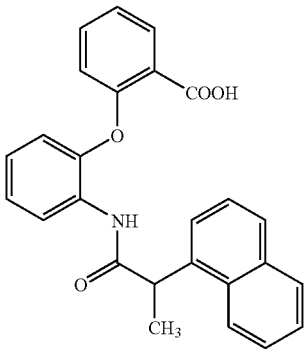

TLC: Rf 0.31 (n-hexane:ethyl acetate=2:3); NMR (DMSO-$d_6$): δ 13.13 (br, 1H), 9.68 (s, 1H), 8.10–8.02 (m, 2H), 7.89 (m, 1H), 7.77 (d, J=7.8 Hz, 1H), 7.72 (dd, J=7.8, 1.8 Hz, 1H), 7.50–7.37 (m, 5H), 7.19 (m, 1H), 7.14–7.03 (m, 2H), 6.89 (dd, J=7.8, 1.8 Hz, 1H), 6.85 (d, J=7.8 Hz, 1H), 4.70 (q, J=7.2 Hz, 1H), 1.50 (d, J=7.2 Hz, 3H).

Example 2(17)

3-[2-[2-(1-naphthyl)propanoylamino]phenylmethyl]thiophen-2-carboxylic acid

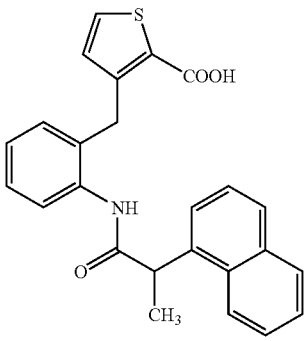

TLC: Rf 0.39 (n-hexane:ethyl acetate=1:2); NMR (DMSO-$d_6$): δ 13.05 (brs, 1H), 9.62 (brs, 1H), 8.25 (m, 1H), 7.92 (m, 1H), 7.80 (d, J=8.1 Hz, 1H), 7.62 (d, J=5.1 Hz, 1H), 7.58–7.42 (m, 4H), 7.37 (m, 1H), 7.17 (m, 1H), 7.07 (m, 1H), 7.00 (dd, J=7.8, 1.5 Hz, 1H), 6.62 (d, J=5.1 Hz, 1H), 4.66 (q, J=7.2 Hz, 1H), 4.27 (d, J=16.2 Hz, 1H), 4.20 (d, J=16.2 Hz, 1H), 1.52 (d, J=7.2 Hz, 3H).

Example 2(18)

(dl)-trans-2-[2-[2-(1-naphthyl)propanoylamino]phenylmethyl]cyclohexanecarboxylic acid

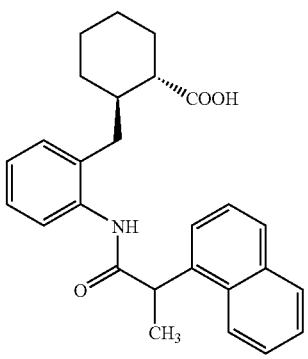

TLC: Rf 0.30 (n-hexane:ethyl acetate=2:1); NMR (DMSO-$d_6$): δ 12.29 (brs, 1H), 9.30 and 9.28 (brs ×2, 1H), 8.40–8.30 (m, 1H), 7.98–7.90 (m, 1H), 7.88–7.80 (m, 1H), 7.65–7.38 (m, 5H), 7.18–7.02 (m, 3H), 4.80–4.64 (m, 1H), 2.62–2.50 (m, 1H), 2.20–2.05 (m, 1H), 1.90–0.78 (m, 12H), 0.60–0.20 (m, 1H).

Example 2(19)

2-[4-fluoro-2-[2-(1-naphthyl)propanoylamino]phenylmethyl]benzoic acid

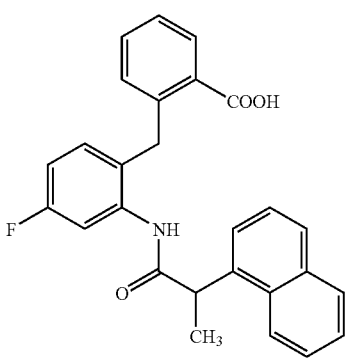

TLC: Rf 0.62 (chloroform:methanol=10:1); NMR (DMSO-$d_6$): δ 9.73 (s, 1H), 8.19 (m, 1H), 8.00–7.82 (m, 3H), 7.60–7.32 (m, 7H), 7.02–6.94 (m, 3H), 4.73 (q, J=6.9 Hz, 1H), 4.33 (d, J=16.8 Hz, 1H), 4.27 (d, J=16.8 Hz, 1H), 1.54 (d, J=6.9 Hz, 3H).

Example 2(20)

2-[4-trifluoromethyl-2-[2-(1-naphthyl)propanoylamino]phenylmethyl]benzoic acid

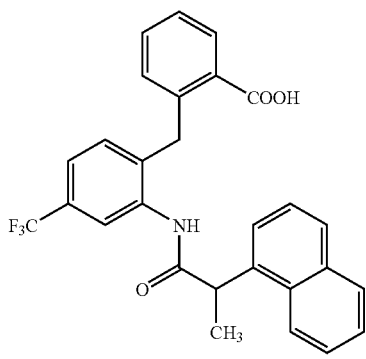

TLC: Rf 0.66 (chloroform:methanol=10:1); NMR (DMSO-$d_6$): δ 9.90 (s, 1H), 8.22 (m, 1H), 8.02–7.85 (m, 4H), 7.63–7.36 (m, 7H), 7.07 (m, 2H), 4.78 (q, J=6.9 Hz, 1H), 4.43 (d, J=16.2 Hz, 1H), 4.36 (d, J=16.2 Hz, 1H), 1.58 (d, J=6.9 Hz, 3H).

Example 2(21)

2-[4-methyl-2-[2-(1-naphthyl)propanoylamino]phenylmethyl]benzoic acid

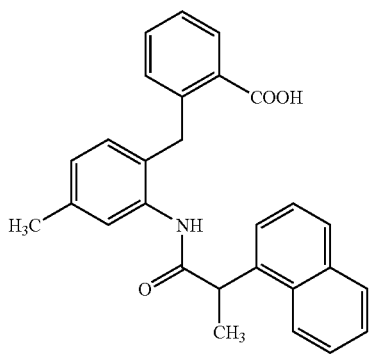

TLC: Rf 0.73 (chloroform:methanol=9:1); NMR (DMSO-$d_6$): δ 9.52 (s, 1H), 8.20 (m, 1H), 7.93–7.74 (m, 3H), 7.55–7.22 (m, 7H), 6.88 (m, 2H), 6.78 (d, J=7.8 Hz, 1H), 4.61 (q, J=6.9 Hz, 1H), 4.23 (d, J=16.5 Hz, 1H), 4.16 (d, J=16.5 Hz, 1H), 2.22 (s, 3H), 1.46 (d, J=6.9 Hz, 3H)

Example 2(22)

(dl)-trans-2-[2-(2-phenylcyclopropylcarbonylamino)phenylmethyl]benzoic acid

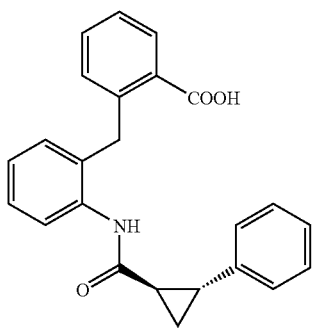

TLC: Rf 0.57 (chloroform:methanol=9:1); NMR (DMSO-$d_6$): δ 9.66 (s, 1H), 7.79 (dd, J=7.8, 1.2 Hz, 1H), 7.58–6.83 (m, 12H), 4.33 (s, 2H), 2.33–2.12 (m, 2H), 1.45–1.21 (m, 2H).

Example 2(23)

2-[2-[2-(4-benzyloxyphenyl)acetylamino]phenylmethyl]benzoic acid

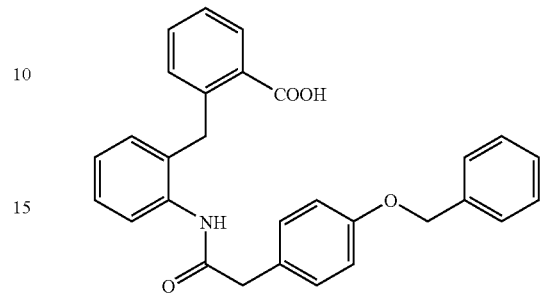

TLC: Rf 0.54 (chloroform:methanol=9:1); NMR (DMSO-$d_6$): δ 9.47 (s, 1H), 7.83 (dd, J=8.7, 1.8 Hz, 1H), 7.50–6.86 (m, 16H), 5.05 (s, 2H), 4.30 (s, 2H), 3.51 (s, 2H)

Example 2(24)

2-[2-(9-oxofluorenoxofluoren-4-ylcarbonylamino)phenylmethyl]benzoic acid

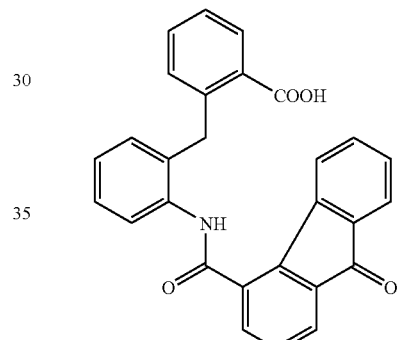

TLC: Rf 0.57 (chloroform:methanol=9:1); NMR (DMSO-$d_6$): δ 10.3 (s, 1H), 7.83–6.98 (m, 15H), 4.42 (s, 2H).

Example 2(25)

2-[2-[5-(4-chlorophenyl)-2-methylfuran-3-ylcarbonylamino]phenylmethyl]benzoic acid

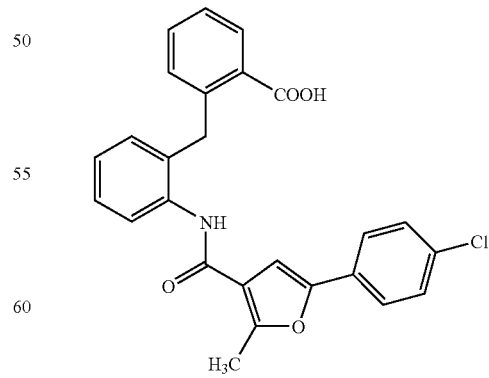

TLC: Rf 0.55 (chloroform:methanol=10:1); NMR (DMSO-$d_6$): δ 9.46 (s, 1H), 7.80 (d, J=7.2 Hz, 1H), 7.65 (d, J=8.7 Hz, 2H), 7.50 (d, J=8.7 Hz, 2H), 7.44–7.37 (m, 2H), 7.32–7.04 (m, 5H), 6.95 (m, 1H), 4.38 (s, 2H), 2.55 (s, 3H).

Example 2(26)

2-[3-[2-(1-naphthyl)propanoylamino]pyridin-2-ylmethyl]benzoic acid

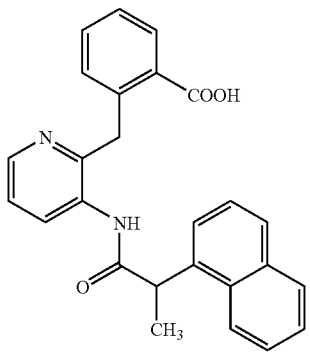

TLC: Rf 0.20 (chloroform:methanol=10:1); NMR (DMSO-d$_6$): δ 9.86 (s, 1H), 8.18 (d, J=7.5 Hz, 1H), 7.97–7.77 (m, 4H), 7.58–7.30 (m, 7H), 7.00–6.93 (m, 2H), 4.71 (q, J=6.9 Hz, 1H), 4.35 (d, J=16.5 Hz, 1H), 4.28 (d, J=16.5 Hz, 1H), 1.50 (d, J=6.9 Hz, 3H).

Example 2(27)

2-[4-cyano-2-[2-(1-naphthyl)propanoylamino]phenylmethyl]benzoic acid

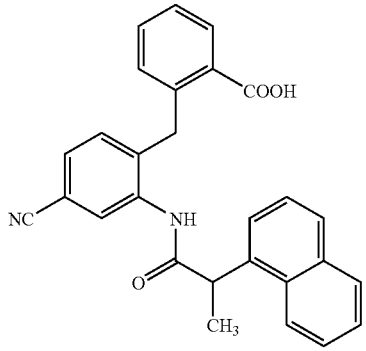

TLC: Rf 0.50 (chloroform:methanol=10:1); NMR (DMSO-d$_6$): δ 10.1 (s, 1H), 8.42–8.13 (m, 3H), 7.96–7.78 (m, 3H), 7.63–7.30 (m, 7H), 6.91 (d, J=6.6 Hz, 1H), 4.68 (q, J=6.9 Hz, 1H), 4.61 (s, 2H), 1.46 (d, J=6.9 Hz, 3H).

Example 2(28)

4-[2-[2-(1-naphthyl)propanoylamino]phenylmethyl]nicotinic acid

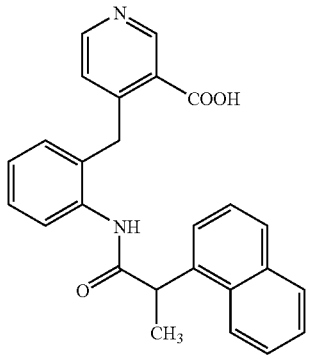

TLC: Rf 0.38 (chloroform:methanol=4:1); NMR (DMSO-d$_6$): δ 13.36 (br, 1H), 9.60 (s, 1H), 8.90 (s, 1H), 8.40 (d, J=5.1 Hz, 1H), 8.15 (m, 1H), 7.89 (m, 1H), 7.77 (d, J=7.5 Hz, 1H), 7.52–7.35 (m, 5H), 7.23 (m, 1H), 7.11 (m, 1H), 7.01 (m, 1H), 6.75 (d, J=5.1 Hz, 1H), 4.56 (q, J=6.9 Hz, 1H), 4.33 (d, J=17.1 Hz, 1H), 4.27 (d, J=17.1 Hz, 1H), 1.42 (d, J=6.9 Hz, 3H).

Example 2(29)

2-[2-[2-(1-naphthyl)propanoylamino]phenylmethyl]nicotinic acid

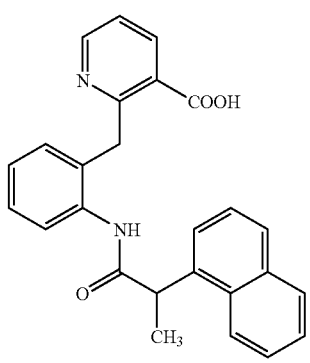

TLC: Rf 0.36 (chloroform:methanol=9:1); NMR (DMSO-d$_6$): δ 13.45 (br, 1H), 10.30 (s, 1H), 8.25 (d, J=8.1 Hz, 1H), 8.08 (dd, J=7.8, 1.8 Hz, 1H), 8.02 (dd, J=4.8, 1.8 Hz, 1H), 7.91 (m, 1H), 7.79 (d, J=8.1 Hz, 1H), 7.68–7.44 (m, 5H), 7.23 (dd, J=7.8, 4.8 Hz, 1H), 7.18–7.10 (m, 2H), 6.96 (m, 1H), 4.70 (q, J=6.9 Hz, 1H), 4.19 (d, J=14.4 Hz, 1H), 4.12 (d, J=14.4 Hz, 1H), 1.63 (d, J=6.9 Hz, 3H).

Example 2(30)

2-[3-[2-(1-naphthyl)propanoylamino]pyridin-4-ylmethyl]benzoic acid

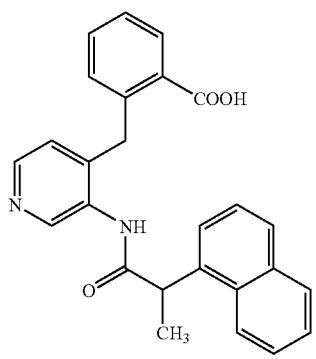

TLC: Rf 0.50 (chloroform:methanol=6:1); NMR (DMSO-d$_6$) δ 10.3 (s, 1H), 8.98 (s, 1H), 8.38 (d, J=6.0 Hz, 1H), 8.23 (d, J=8.1 Hz, 1H), 7.93 (m, 2H), 7.83 (d, J=7.8 Hz, 1H), 7.60–7.39 (m, 6H), 7.17 (d, J=7.8 Hz, 1H), 7.07 (d, J=5.4 Hz, 1H), 4.84 (q, J=6.9 Hz, 1H), 4.46 (d, J=17.1 Hz, 1H), 4.38 (d, J=17.1 Hz, 1H), 1.56 (d, J=6.9 Hz, 3H).

REFERENCE EXAMPLE 5

2-(4-cyano-2-nitrophenylmethyl)benzoic acid methyl ester

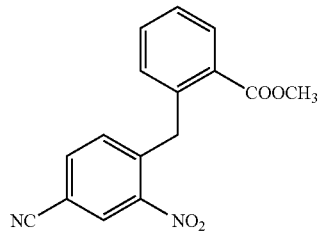

Under atmosphere of argon, to a solution of zinc powder (1.89 g) in anhydrous THF (15 ml) was added dibromoethane (116 μl) and the mixture was stirred for five minutes at 60° C. To the reaction mixture was added a solution of 2-bromomethylbenzoic acid methyl ester (4.42 g) in anhydrous THF (15 ml) over a period of 30 minutes at 0° C. and the mixture was stirred for 2 hours at the temperature to give a 2-carbomethoxybenzylzinc (II) bromide (benzyl zinc) solution.

Under atmosphere of argon, to a solution of 1-cyano-3-nitro-4-iodobenzene (2.00 g), bis(dibenzylideneacetone)palladium (42 mg) and 1,1'-bis(diphenylphosphino)ferrocene (41 mg) in anhydrous THF (10 ml) was added the above prepared benzyl zinc solution dropwise at room temperature and the mixture was stirred for 2 hours at 60° C. To the reaction mixture was added a saturated aqueous solution of ammonium chloride at 0° C. and was extracted with ethyl acetate. The organic layer was washed with water and a saturated aqueous solution of sodium chloride and was dried over magnesium sulfate and was concentrated. The residue was purified by column chromatography on silica gel (n-hexane:ethyl acetate=5:1) to give the title compound (809 mg) having the following physical data.

TLC: Rf 0.61 (n-hexane:ethyl acetate=2:1); NMR (CDCl$_3$): δ 8.25 (d, J=1.8 Hz, 1H), 8.05 (dd, J=7.8, 1.5 Hz, 1H), 7.66 (dd, J=8.0, 1.8 Hz, 1H), 7.54 (dt, J=7.8, 1.5 Hz, 1H), 7.42 (dt, J=7.8, 1.5 Hz, 1H), 7.23 (d, J=7.8 Hz, 1H), 7.10 (d, J=8.0 Hz, 1H), 4.69 (s, 2H), 3.76 (s, 3H)

REFERENCE EXAMPLE 6

2-(2-amino-4-cyanophenylmethyl)benzoic acid methyl ester

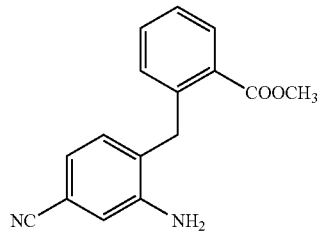

To a solution of the compound prepared in reference example 5 (705 mg) in acetic acid/water (7 ml/0.7 ml) was added steel (664 mg) and the mixture was stirred for 20 minutes at 60° C. To the reaction mixture was added water at 0° C. and was filtered over celite (brand name). The filtrate was washed with water, a saturated aqueous solution of sodium bicarbonate and a saturated aqueous solution of sodium chloride, dried over magnesium sulfate and was concentrated. The residue was purified by column chromatography on silica gel (hexane:ethyl acetate=6:1~4:1) to give the title compound (355 mg) having the following physical data.

TLC: Rf 0.40 (n-hexane:ethyl acetate=2:1); NMR (CDCl$_3$): δ 7.93 (dd, J=7.7, 1.4 Hz, 1H), 7.44 (dt, J=7.7, 1.4 Hz, 1H), 7.32 (dt, J=7.7, 1.4 Hz, 1H), 7.14 (d, J=7.8 Hz, 1H), 7.02–6.94 (m, 2H), 6.89 (s, 1H), 4.25 (s, 2H), 4.13 (bs, 2H), 3.88 (s, 3H).

EXAMPLE 3

2-[4-cyano-2-[4-methyl-2-(1-naphthyl)pentanoylamino]phenylmethyl]benzoic acid methyl ester

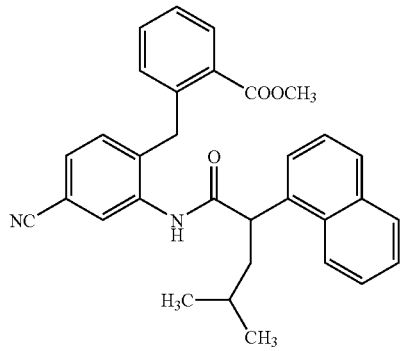

Under atmosphere of argon, the compound prepared in reference example 6 (213 mg) and pyridine (129 μl) in anhydrous methylene chloride (2 ml) was added 4-methyl-2-(1-naphthyl)valeryl chloride (250 mg) in anhydrous methylene chloride (1 ml) at 0° C. and the mixture was stirred for 15 minutes at the temperature. To the reaction mixture was added a saturated aqueous solution of sodium bicarbonate at 0° C. and was extracted with ethyl acetate. The organic layer was washed with water and a saturated aqueous solution of sodium chloride and was dried over sodium sulfate and was concentrated. The residue was purified by column chromatography on silica gel (n-hexane:ethyl acetate=9:1~3:1) to give the title compound (371 mg) having the following physical data.

TLC: Rf 0.60 (n-hexane:ethyl acetate=2:1); NMR (CDCl$_3$): δ 8.56 (bs, 1H), 8.07 (d, J=7.8 Hz, 1H), 7.85 (m, 1H), 7.69 (d, J=7.8 Hz, 1H), 7.58–7.45 (m, 2H), 7.37–7.21 (m, 6H), 7.18–7.05 (m, 2H), 6.87 (d, J=7.8 Hz, 1H), 4.42 (dd, J=8.7, 5.4 Hz, 1H), 4.10 (d, J=16 Hz, 1H), 3.87 (d, J=16 Hz, 1H), 3.73 (s, 3H), 2.17 (m, 1H), 1.75–1.59 (m, 2H), 1.01 (d, J=6.3 Hz, 3H), 0.92 (d, J=6.3 Hz, 3H).

EXAMPLE 4

2-[4-cyano-2-[4-methyl-2-(1-naphthyl)pentanoylamino]phenylmethyl]benzoic acid

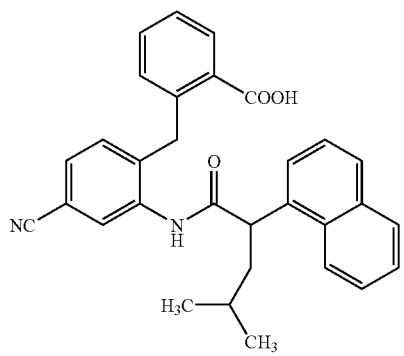

To a solution of the compound prepared in example 3 (365 mg) in THF/methanol (2 ml/1 ml) was added 1N aqueous solution of sodium hydroxide (1 ml) and the mixture was stirred for 4 hours at room temperature. The reaction mixture was concentrated and the residue was diluted with ether and was extracted with water. The aqueous layer was neutralized with 1N hydrochloric acid and was extracted with ethyl acetate. The organic layer was washed with water and a saturated aqueous solution of sodium chloride, dried over magnesium sulfate and was concentrated. The residue was purified by column chromatography on silica gel (chloroform~chloroform:methanol=50:1) to give the title compound (313 mg) having the following physical data.

TLC: Rf 0.60 (chloroform:methanol=9:1); NMR (CDCl$_3$): δ 8.51 (s, 1H), 8.03 (d, J=7.8 Hz, 1H), 7.95 (s, 1H), 7.82 (m, 1H), 7.68 (d, J=7.8 Hz, 1H), 7.61 (d, J=7.5 Hz, 1H), 7.53–7.40 (m, 2H), 7.36–7.06 (m, 6H), 6.79 (d, J=7.5 Hz, 1H), 4.37 (t, J=7.4 Hz, 1H), 4.09 (d, J=16 Hz, 1H), 3.83 (d, J=16 Hz, 1H), 2.18 (m, 1H), 1.80–1.54 (m, 2H), 0.98 (d, J=6.6 Hz, 3H), 0.91 (d, J=6.6 Hz, 3H).

Example 4(1)~Example 4(34)

By the same procedure as described in Reference Example 5>Reference Example 6>Example 3>Example 4 using the corresponding compounds, optionally followed by converting to known salts, the following compounds were given.

Example 4(1)

2-[2-[2-(4-benzyloxyphenyl)propanoylamino]phenylmethyl]benzoic acid

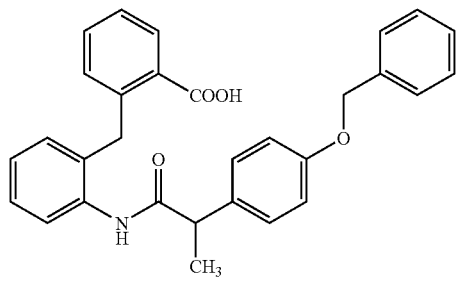

TLC: Rf 0.25 (n-hexane:ethyl acetate=1:2); NMR (CDCl$_3$): δ 8.01–7.97 (m, 2H), 7.47 (brs, 1H), 7.43–7.23 (m, 8H), 7.07–7.04 (m, 4H), 6.93 (d, J=7.8 Hz, 1H), 6.80 (d, J=8.4 Hz, 2H), 5.00 (s, 2H), 4.15 (d, J=17.3 Hz, 1H), 4.14 (d, J=17.3 Hz, 1H), 3.58 (q, J=7.2 Hz, 1H), 1.45 (d, J=7.2 Hz, 3H).

Example 4(2)

2-[2-[2-(3-benzyloxyphenyl)propanoylamino]phenylmethyl]benzoic acid

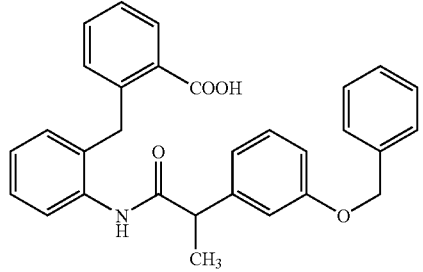

TLC: Rf 0.30 (n-hexane:ethyl acetate=1:2); NMR (CDCl$_3$): δ 7.96 (d, J=8.1 Hz, 2H), 7.61 (brs, 1H), 7.40–7.22 (m, 8H), 7.11–7.04 (m, 3H), 6.98 (d, J=7.5 Hz, 1H), 6.86 (s, 1H), 6.80–6.75 (m, 2H), 4.96 (s, 2H), 4.15 (d, J=16.5 Hz, 1H), 4.13 (d, J=16.5 Hz, 1H), 3.61 (q, J=7.2 Hz, 1H), 1.47 (d, J=7.2 Hz, 3H).

Example 4(3)

2-[2-[2-(1-naphthyl)butanoylamino]phenylmethyl]benzoic acid

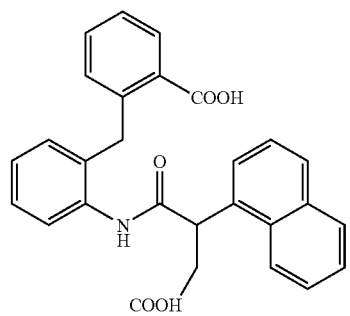

TLC: Rf 0.45 (n-hexane:ethyl acetate=1:2); NMR (CDCl$_3$): δ 8.02 (d, J=7.5 Hz, 2H), 7.80–7–72 (m, 2H), 7.66 (d, J=8.1 Hz, 1H), 7.56 (brs, 1H), 7.45–7.40 (m, 2H), 7.32–7.14 (m, 5H), 7.07–7.00 (m, 2H), 6.80 (d, J=7.5 Hz, 1H), 4.13 (t, J=7.2 Hz, 1H), 4.05 (d, J=16.8 Hz, 1H), 3.87 (d, J=16.8 Hz, 1H), 2.34–2.25 (m, 1H), 1.98–1.89 (m, 1H), 0.95 (t, J=7.2 Hz, 3H).

Example 4(4)

2-[2-[2-(1-naphthyl)pentanoylamino]phenylmethyl]benzoic acid

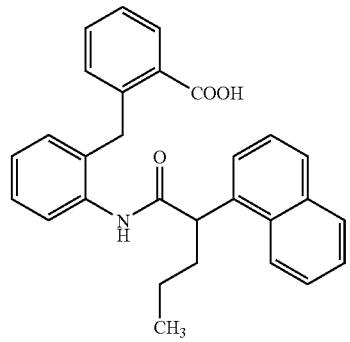

TLC: Rf 0.50 (n-hexane:ethyl acetate=1:2); NMR (CDCl$_3$): δ 8.03 (d, J=8.7 Hz, 2H), 7.81–7–77 (m, 1H), 7.73 (d, J=6.6 Hz, 1H), 7.66 (d, J=8.1 Hz, 1H), 7.57 (brs, 1H), 7.45–7.41 (m, 2H), 7.32–7.14 (m, 5H), 7.07–7.00 (m, 2H), 6.80 (d, J=7.5 Hz, 1H), 4.23 (t, J=7.4 Hz, 1H), 4.05 (d, J=17.0 Hz, 1H), 3.87 (d, J=17.0 Hz, 1H), 2.30–2.18 (m, 1H), 1.92–1.80 (m, 1H), 1.40–1.28 (m, 2H), 0.90 (t, J=7.4 Hz, 3H).

Example 4(5)

2-[2-[3-methyl-2-(1-naphthyl)butanoylamino]phenylmethyl]benzoic acid

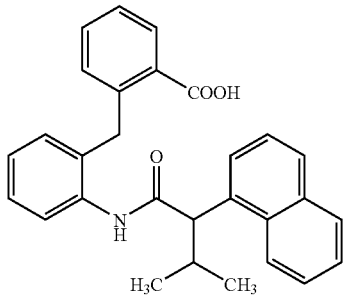

TLC: Rf 0.50 (n-hexane:ethyl acetate=1:2); NMR (CDCl$_3$): δ 8.13 (d, J=7.8 Hz, 1H), 7.93 (d, J=8.1 Hz, 1H), 7.81–7–66 (m, 4H), 7.55 (d, J=7.5 Hz, 1H), 7.47–7.39 (m, 2H), 7.36–7.17 (m, 4H), 7.04–7.03 (m, 2H), 6.90 (d, J=7.5 Hz, 1H), 4.15 (d, J=16.5 Hz, 1H), 4.02 (d, J=16.5 Hz, 1H), 3.91 (d, J=9.9 Hz, 1H), 2.62–2.50 (m, 1H), 1.13 (d, J=6.6 Hz, 3H), 0.70 (d, J=6.6 Hz, 3H).

Example 4(6)

2-[2-[2-(1,1'-biphenyl-2-yl)propanoylamino]phenylmethyl]benzoic acid

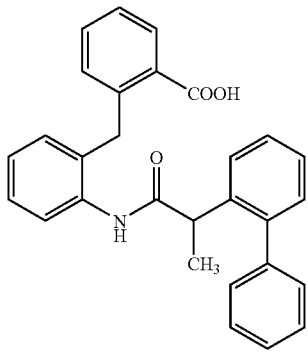

TLC: Rf 0.40 (n-hexane:ethyl acetate=1:2); NMR (CDCl$_3$): δ 8.07 (dd, J=7.5, 1.5 Hz, 1H), 7.90 (d, J=8.1 Hz, 1H), 7.40–6.96 (m, 15H), 6.87 (d, J=7.5 Hz, 1H), 4.07 (s, 2H), 3.78 (q, J=6.9 Hz, 1H), 1.44 (d, J=6.9 Hz, 3H)

Example 4(7)

2-[2-[2-(1,1'-biphenyl-3-yl)propanoylamino]phenylmethyl]benzoic acid

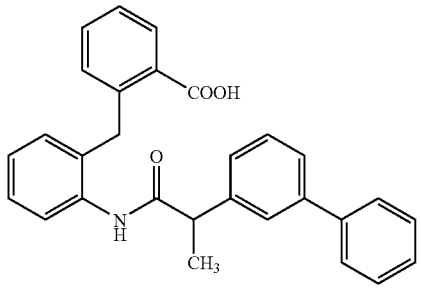

TLC: Rf 0.25 (n-hexane:ethyl acetate=1:2); NMR (CDCl$_3$): δ 7.98 (d, J=7.8 Hz, 1H), 7.89 (d, J=7.8 Hz, 1H), 7.66 (br s, 1H), 7.51–7.04 (m, 14H), 6.97 (d, J=7.5 Hz, 1H), 4.20 (d, J=16.5 Hz, 1H), 4.10 (d, J=16.5 Hz, 1H), 3.71 (q, J=7.2 Hz, 1H), 1.53 (d, J=7.2 Hz, 3H).

Example 4(8)

2-[2-[2-(4-phenoxyphenyl)propanoylamino]phenylmethyl]benzoic acid

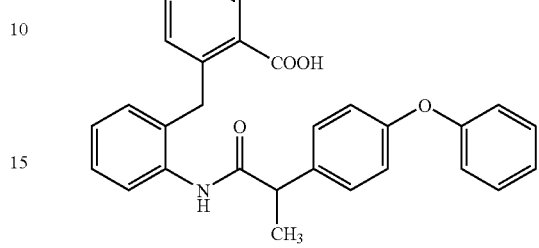

TLC: Rf 0.20 (n-hexane:ethyl acetate=1:2); NMR (CDCl$_3$): δ 7.99 (d, J=8.1 Hz, 1H), 7.94 (d, J=7.8 Hz, 1H), 7.70 (br s, 1H), 7.42 (t, J=7.5 Hz, 1H), 7.32–6.91 (m, 13H), 6.80 (d, J=6.9 Hz, 1H), 4.17 (s, 2H), 3.61 (q, J=7.2 Hz, 1H), 1.46 (d, J=7.2 Hz, 3H).

Example 4(9)

2-[2-[2-[4-(2-phenylethoxy)phenyl]propanoylamino]phenylmethyl]benzoic acid

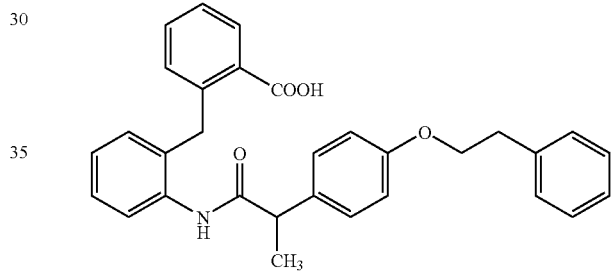

TLC: Rf 0.40 (n-hexane:ethyl acetate=1:3); NMR (CDCl$_3$): δ 7.99 (d, J=8.1 Hz, 1H), 7.95 (d, J=8.1 Hz, 1H), 7.42 (brs, 1H), 7.27–7.19 (m, 9H), 7.06–7.01 (m, 3H), 6.89 (d, J=7.2 Hz, 1H), 6.70 (d, J=8.4 Hz, 2H), 4.20–4.07 (m, 4H), 3.56 (q, J=7.2 Hz, 1H), 3.06 (t, J=6.9 Hz, 2H), 1.44 (d, J=7.2 Hz, 3H).

Example 4(10)

2-[2-[2-[4-(3-phenylpropoxy)phenyl]propanoylamino]phenylmethyl]benzoic acid

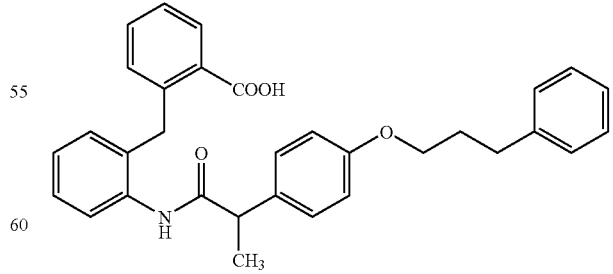

TLC: Rf 0.45 (n-hexane:ethyl acetate=1:3); NMR (CDCl$_3$): δ 7.98 (d, J=8.1 Hz, 2H), 7.45 (brs, 1H), 7.37 (dt, J=1.5, 7.5 Hz, 1H), 7.31–7.18 (m, 8H), 7.06–7.03 (m, 3H), 6.92 (d, J=8.1 Hz, 1H), 6.70 (d, J=8.4 Hz, 2H), 4.16 (d, J=17.1 Hz, 1H), 4.14 (d, J=17.1 Hz, 1H), 3.88 (t, J=6.3 Hz, 2H), 3.57 (q, J=7.2 Hz, 1H), 2.70 (t, J=7.8 Hz, 2H), 2.12–2.02 (m, 2H), 1.44 (d, J=7.2 Hz, 3H).

Example 4(11)

2-[2-[2-methoxy-2-(1-naphthyl)acetylamino]phenyl-methyl]benzoic acid

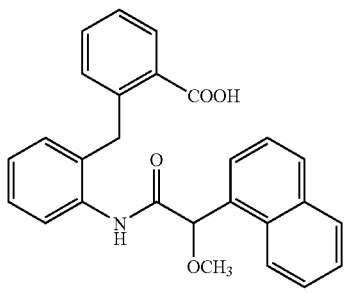

TLC: Rf 0.30 (n-hexane:ethyl acetate=1:3); NMR (CDCl$_3$): δ 8.66 (brs, 1H), 8.17–8.12 (m, 2H), 8.04 (d, J=8.1 Hz, 1H), 7.82–7–75 (m, 2H), 7.52–7.31 (m, 6H), 7.25–7.21 (m, 1H), 7.10–7.08 (m, 3H), 5.25 (s, 1H), 4.51 (s, 2H), 3.24 (s, 3H).

Example 4(12)

2-[2-[2-(4-isobutylphenyl)propanoylamino]phenylm-ethyl]benzoic acid

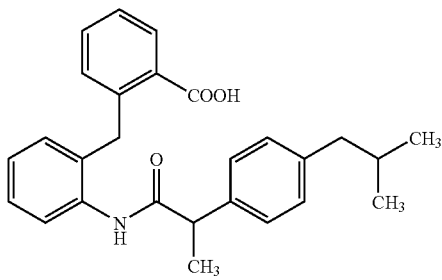

TLC: Rf 0.55 (ethyl acetate); NMR (CDCl$_3$): δ 8.02 (dd, J=7.8, 1.2 Hz, 1H), 7.96 (d, J=7.5 Hz, 1H), 7.50 (brs, 1H), 7.40 (dt, J=1.5, 7.5 Hz, 1H), 7.33–7.21 (m, 2H), 7.10–6.98 (m, 7H), 4.12 (s, 2H), 3.62 (q, J=6.9 Hz, 1H), 2.39 (d, J=6.9 Hz, 2H), 1.81–1.72 (m, 1H), 1.48 (d, J=6.9 Hz, 3H), 0.82 (d, J=6.6 Hz, 6H).

Example 4(13)

2-[2-[4-methyl-2-(1-naphthyl)pentanoylamino]phe-nylmethyl]benzoic acid

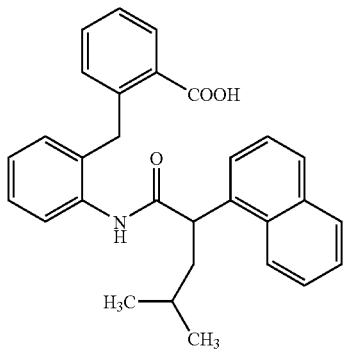

TLC: Rf 0.35 (n-hexane:ethyl acetate=1:1); NMR (CDCl$_3$): δ 8.08–8.03 (m, 2H), 7.82–7.62 (m, 4H), 7.49–7.41 (m, 2H), 7.33–7.18 (m, 4H), 7.17–6.95 (m, 3H), 6.81 (d, J=7.5 Hz, 1H), 4.34 (brt, 1H), 4.08 (d, J=16.5 Hz, 1H), 3.84 (d, J=16.5 Hz, 1H), 2.20–2.12 (m, 1H), 1.77–1.69 (m, 1H) 1.64–1.56 (m, 1H), 0.95 (d, J=6.5 Hz, 3H), 0.88 (d, J=6.5 Hz, 3H).

Example 4(14)

2-[2-[2-(1-naphthyl)hexanoylamino]phenylmethyl]benzoic acid

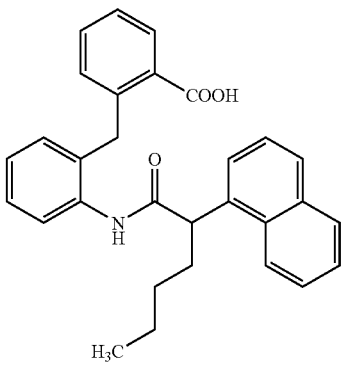

TLC: Rf 0.34 (n-hexane:ethyl acetate=1:1); NMR (CDCl$_3$): δ 8.04 (d, J=8.0 Hz, 2H), 7.80 (d, J=7.0 Hz, 1H), 7.72–7.60 (m, 3H), 7.49–7.39 (m, 2H), 7.32–7.14 (m, 5H), 7.07–7.00 (m, 2H), 6.81 (d, J=7.5 Hz, 1H), 4.21 (t, J=7.5 Hz, 1H), 4.13 (d, J=16.5 Hz, 1H), 3.86 (d, J=16.5 Hz, 1H), 2.33–2.19 (m, 1H), 1.94–1.79 (m, 1H), 1.40–1.20 (m, 4H), 0.84 (t, J=7.0 Hz, 3H).

Example 4(15)

2-[2-[2-[4-(4-phenylbutoxy)phenyl]propanoylamino]phenylmethyl]benzoic acid

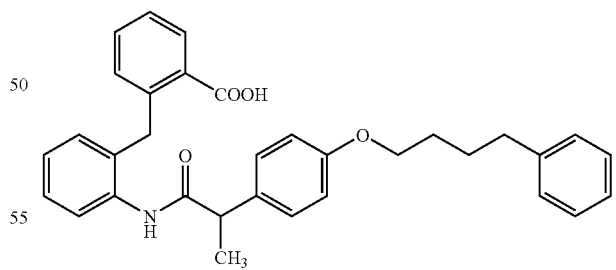

TLC: Rf 0.60 (ethyl acetate); NMR (CDCl$_3$): δ 7.99 (t, J=7.2 Hz, 2H), 7.45 (s, 1H), 7.37 (dt, J=1.5, 7.5 Hz, 1H), 7.30–7.15 (m, 8H), 7.06–7.03 (m, 3H), 6.92 (d, J=7.5 Hz, 1H), 6.69 (d, J=8.4 Hz, 2H), 4.16 (d, J=17.1 Hz, 1H), 4.15 (d, J=17.1 Hz, 1H), 3.88 (m, 2H), 3.57 (q, J=6.9 Hz, 1H), 2.66 (m, 2H), 1.77 (m, 4H), 1.44 (d, J=6.9 Hz, 3H).

Example 4(16)

2-[2-[2(R)-(1-naphthyl)propanoylamino]phenylmethyl]benzoic acid

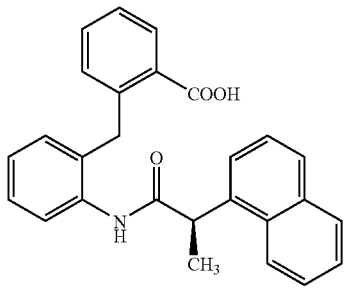

TLC: Rf 0.40 (ethyl acetate); NMR (CDCl$_3$): δ 8.00 (d, J=8.1 Hz, 2H), 7.82–7.76 (m, 2H), 7.66 (d, J=7.5 Hz, 1H), 7.45–7.39 (m, 3H), 7.31–7.16 (m, 5H), 7.06–6.95 (m, 2H), 6.77 (d, J=7.2 Hz, 1H), 4.40 (q, J=7.2 Hz, 1H), 3.94 (d, J=16.8 Hz, 1H), 3.81 (d, J=16.8 Hz, 1H), 1.66 (d, J=7.2 Hz, 3H).

Example 4(17)

2-[2-[2(S)-(1-naphthyl)propanoylamino]phenylmethyl]benzoic acid

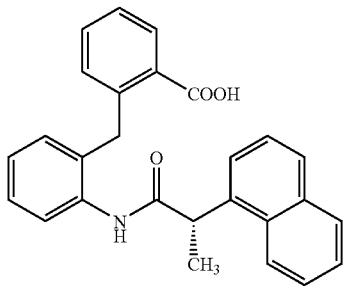

TLC: Rf 0.40 (ethyl acetate); NMR (CDCl$_3$): δ 8.04–8.00 (m, 2H), 7.81–7.75 (m, 2H), 7.67 (d, J=9.0 Hz, 1H), 7.47–7.42 (m, 3H), 7.28–7.16 (m, 5H), 7.06–6.97 (m, 2H), 6.79 (d, J=7.8 Hz, 1H), 4.41 (q, J=7.2 Hz, 1H), 3.96 (d, J=16.8 Hz, 1H), 3.81 (d, J=16.8 Hz, 1H), 1.65 (d, J=7.2 Hz, 3H).

Example 4(18)

2-[4-cyano-2-[4-methyl-2-(1-naphthyl)pentanoylamino]phenylmethyl]benzoic acid sodium salt

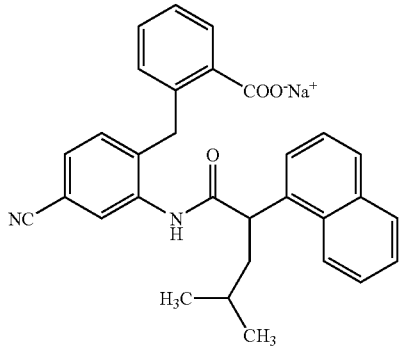

TLC: Rf 0.60 (chloroform:methanol=9:1); NMR (DMSO-d$_6$): δ 8.63 (d, J=8.4 Hz, 1H), 8.50 (s, 1H), 7.84 (m, 1H), 7.73 (d, J=7.8 Hz, 1H), 7.65–7.36 (m, 8H), 6.98 (m, 2H), 6.87 (m, 1H), 5.16 (m, 1H), 4.61 (d, J=14.4 Hz, 1H), 4.22 (d, J=14.4 Hz, 1H), 1.60 (m, 2H), 1.31 (m, 1H), 0.84 (d, J=6.3 Hz, 3H), 0.73 (d, J=6.3 Hz, 3H).

Example 4(19)

2-[2-[2-ethoxy-2-(1-naphthyl)acetylamino]phenylmethyl]benzoic acid

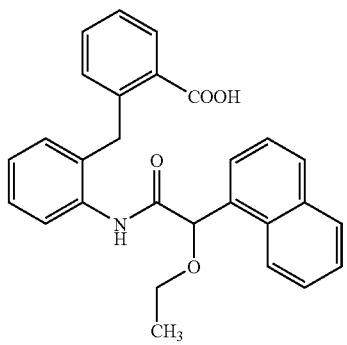

TLC: Rf 0.18 (n-hexane:ethyl acetate=3:1); NMR (CDCl$_3$): δ 8.77 (brs, 1H), 8.22–8.17 (m, 2H), 8.06 (d, J=7.8 Hz, 1H), 7.82–7.73 (m, 2H), 7.54–7.21(m, 6H), 7.13–7.03 (m, 3H), 5.40 (s, 1H), 4.53 (brs, 2H), 3.49–3.35 (m, 2H), 1.03(t, J=7.2 Hz, 3H).

Example 4(20)

2-[2-[2-(1-naphthyl)heptanoylamino]phenylmethyl]benzoic acid

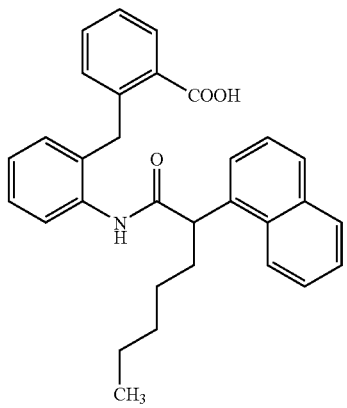

TLC: Rf 0.19 (n-hexane:ethyl acetate=3:1); NMR (CDCl$_3$): δ 8.09–7.98 (m, 2H), 7.80–7.72 (m, 2H), 7.65 (d, J=6.9 Hz, 1H), 7.52 (bs, 1H), 7.49–7.37 (m, 2H), 7.35–7.13 (m, 4H), 7.08–6.97 (m, 2H), 6.79 (d, J=6.9 Hz, 1H), 4.19 (m, 1H), 4.02 (brd, J=17.1 Hz, 1H), 3.88 (brd, J=17.1 Hz, 1H), 2.25 (m, 1H), 1.87 (m, 1H), 1.60–1.10 (m, 5H), 0.88–0.78 (m, 4H).

Example 4(21)

2-[2-[4,4-dimethyl-2-(1-naphthyl)pentanoylamino]phenyl methyl]benzoic acid

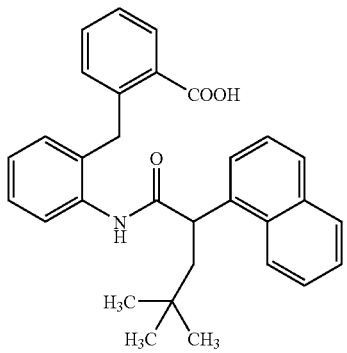

TLC: Rf 0.37 (n-hexane:ethyl acetate=1:1); NMR (CDCl₃): δ 8.10–8.00 (m, 2H), 7.85 (brs, 1H), 7.80 (m, 1H), 7.63 (brd, J=7.8 Hz, 1H), 7.52–7.38 (m, 3H), 7.34 (brd, J=7.6 Hz, 1H), 7.30–7.17 (m, 3H), 7.13–7.02 (m, 3H), 6.83 (brd, J=7.8 Hz, 1H), 4.22 (m, 1H), 4.16 (d, J=16.5 Hz, 1H), 3.85 (d, J=16.5 Hz, 1H), 2.53 (m, 1H), 1.58 (dd, J=13.8, 3.6 Hz, 1H), 0.92 (s, 9H).

Example 4(22)

2-[2-[2-[4-(3-phenylpropyl)phenyl]propanoylamino]phenylmethyl]benzoic acid

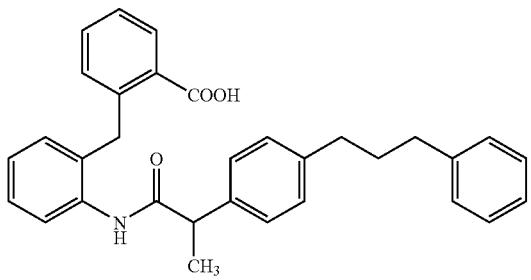

TLC: Rf 0.51 (chloroform:methanol=10:1); NMR (DMSO-d₆): δ 9.41 (s, 1H), 7.79 (d, J=7.2 Hz, 1H), 7.43 (d, J=8.4 Hz, 1H), 7.36–7.00 (m, 13H), 6.89 (d, J=7.5 Hz, 2H), 4.22 (s, 2H), 3.80 (q, J=6.9 Hz, 1H), 2.60–2.40 (m, 4H), 1.82 (m, 2H), 1.30 (d, J=6.9 Hz, 3H).

Example 4(23)

2-[2-[2-(quinolin-5-yl)propanoylamino]phenylmethyl]benzoic acid

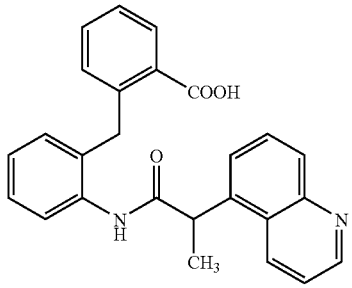

TLC: Rf 0.25 (chloroform:methanol=9:1); NMR (CD₃OD): δ 8.82 (dd, J=4.2, 1.2 Hz, 1H), 8.63 (d, J=8.7 Hz, 1H), 7.90 (d, J=8.4 Hz, 1H), 7.66–7.50 (m, 5H), 7.24–7.18 (m, 2H), 7.14–7.09 (m, 3H), 6.87 (d, J=7.5 Hz, 1H), 4.60 (q, J=7.2 Hz, 1H), 4.25 (d, J=16.5 Hz, 1H), 4.10 (d, J=16.5 Hz, 1H), 1.56 (d, J=7.2 Hz, 3H).

Example 4(24)

2-[2-[2-[4-[2-(3-pyridyl)ethoxy]phenyl]propanoylamino]phenylmethyl]benzoic acid hydrochloride

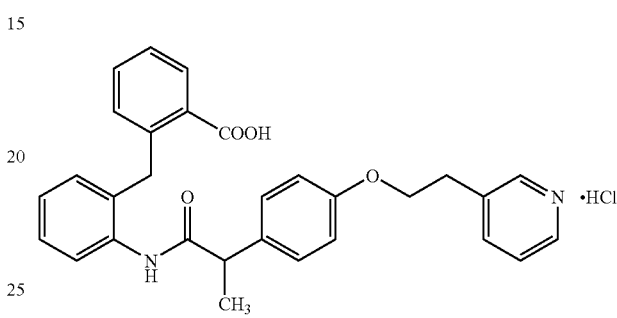

TLC: Rf 0.56 (chloroform:methanol=9:1); NMR (DMSO-d₆): δ 9.39 (brs, 1H), 8.84 (brs, 1H), 8.75 (d, J=5.4 Hz, 1H), 8.42 (d, J=8.0 Hz, 1H), 7.91 (dd, J=8.0, 5.4 Hz, 1H), 7.79 (dd, J=8.0, 1.2 Hz, 1H), 7.42–7.10 (m, 6H), 7.04 (m, 1H), 6.92–6.86 (m, 2H), 6.81 (d, J=8.7 Hz, 2H), 4.25–4.20 (m, 2H), 4.22 (s, 2H), 3.77 (q, J=6.9 Hz, 1H), 3.20 (t, J=6.2 Hz, 2H), 1.28 (d, J=6.9 Hz, 3H).

Example 4(25)

2-[2-[2-[4-(2-phenoxyethyl)phenyl]propanoylamino]phenylmethyl]benzoic acid

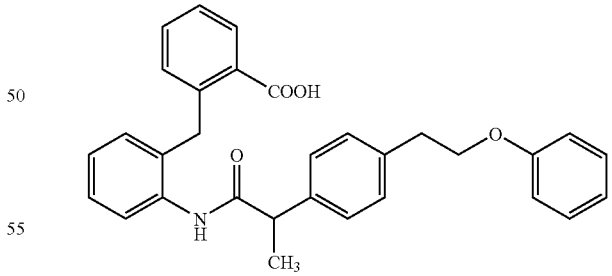

TLC: Rf 0.15 (n-hexane:ethyl acetate=1:1); NMR (CDCl₃): δ 7.99 (dd, J=7.5, 1.2 Hz, 1H), 7.95 (brd, J=8.1 Hz, 1H), 7.55 (brs, 1H), 7.36 (m, 1H), 7.30–7.21 (m, 4H), 7.15–7.02 (m, 6H), 6.98–9.83 (m, 4H), 4.21–4.08 (m, 4H), 3.61 (q, J=7.2 Hz, 1H), 3.01 (t, J=6.9 Hz, 2H), 1.45 (d, J=7.2 Hz, 3H).

Example 4(26)

2-[2-[4-methoxy-2-(1-naphthyl)butanoylamino]phenylmethyl]benzoic acid

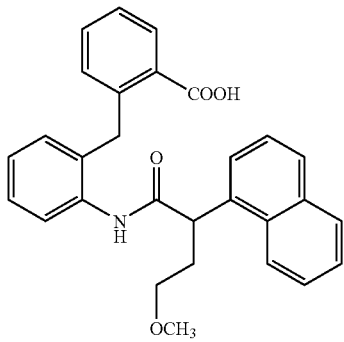

TLC: Rf 0.51 (chloroform:methanol=10:1); NMR (DMSO-d$_6$): δ 9.69 (s, 1H), 8.30 (d, J=8.4 Hz, 1H), 7.91 (d, J=7.5 Hz, 1H), 7.79 (d, J=8.1 Hz, 1H), 7.74 (m, 1H), 7.59–7.19 (m, 6H), 7.15 (t, J=7.5 Hz, 1H), 7.04 (t, J=7.5 Hz, 1H), 6.88 (d, J=8.1 Hz, 1H), 6.84 (d, J=7.8 Hz, 1H), 4.69 (dd, J=8.7, 5.1 Hz, 1H), 4.26 (d, J=15.9 Hz, 1H), 4.18 (d, J=15.9 Hz, 1H), 3.29 (s, 2H), 3.17 (s, 3H), 2.29 (m, 1H), 1.94 (m, 1H).

Example 4(27)

2-[2-[5-methyl-2-(1-naphthyl)hexanoylamino]phenylmethyl]benzoic acid

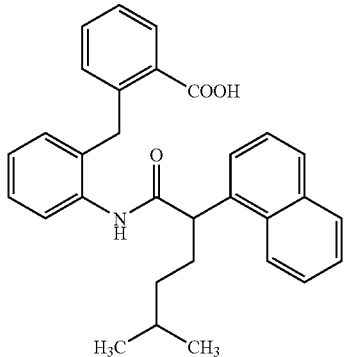

TLC: Rf 0.69 (chloroform:methanol=10:1); NMR (CDCl$_3$): δ 8.04 (d, J=7.8 Hz, 2H), 7.80 (m, 1H), 7.74–7.64 (m, 2H), 7.61 (bs, 1H), 7.45 (m, 2H), 7.34–7.12 (m, 5H), 7.02 (m,2H), 6.82 (d, J=7.8 Hz, 1H) 4.17 (t, J=7.2 Hz, 1H), 4.04 (d, J=16.8 Hz, 1H), 3.87 (d, J=16.8 Hz, 1H), 2.25 (m, 1H), 1.87 (m, 1H), 1.54 (m, 1H), 1.28 (m, 1H), 1.15 (m, 1H), 0.86 (d, J=6.9 Hz, 3H), 0.84 (d, J=6.9 Hz, 3H).

Example 4(28)

5-[2-[2-(1-naphthyl)propanoylamino]phenylmethyl]oxazol-4-carboxylic acid

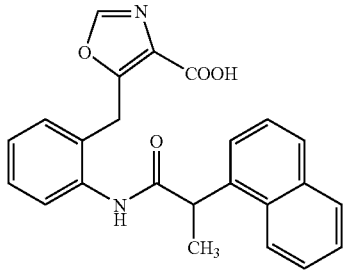

TLC: Rf 0.26 (chloroform:methanol=9:1); NMR (DMSO-d$_6$): δ 13.1 (br, 1H), 9.69 (s, 1H), 8.27 (d, J=8.0 Hz, 1H), 8.24 (s, 1H), 7.93 (dd, J=8.0, 1.8 Hz, 1H), 7.82 (d, J=8.0 Hz, 1H), 7.60–7.45 (m, 4H), 7.29 (dd, J=8.0, 1.2 Hz, 1H), 7.21 (m, 1H), 7.12 (m, 1H), 7.03 (dd, J=8.0, 1.2 Hz, 1H), 4.65 (q, J=7.2 Hz, 1H), 4.33 (d, J=16.5 Hz, 1H), 4.26 (d, J=16.5 Hz, 1H), 1.56 (d, J=7.2 Hz, 3H).

Example 4(29)

2-[2-[2-[4-(2-phenylethylthio)phenyl]propanoylamino]phenylmethyl]benzoic acid

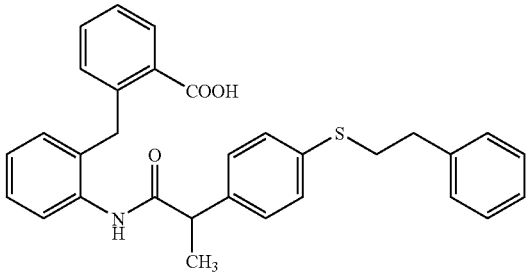

TLC: Rf 0.45 (chloroform:methanol=9:1); NMR (200 MHz, CDCl$_3$): δ 7.98–7.95 (m, 2H), 7.63 (s, 1H), 7.42–6.96 (m, 15H), 4.18 (d, J=16.9 Hz, 1H), 4.16 (d, J=16.9 Hz, 1H), 3.60 (q, J=7.2 Hz, 1H), 3.16–3.07 (m, 2H), 2.92–2.84 (m, 2H), 1.45 (d, J=7.2 Hz, 3H).

Example 4(30)

2-[2-[3-methoxy-2-(1-naphthyl)propanoylamino]phenylmethyl]benzoic acid

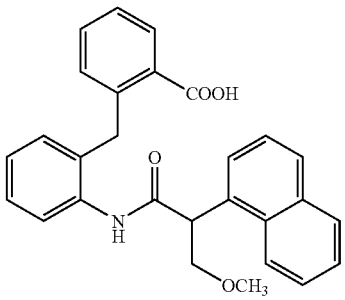

TLC: Rf 0.55 (chloroform:methanol=10:1); NMR (DMSO-d$_6$): δ 9.77 (s, 1H), 8.34 (d, J=8.4 Hz, 1H), 7.95 (d, J=7.8 Hz, 1H), 7.84 (d, J=8.1 Hz, 1H), 7.80–7.72 (m, 1H), 7.66–7.40 (m, 5H), 7.36–7.21 (m, 2H), 7.17 (t, J=7.2 Hz, 1H), 7.06 (t, J=7.2 Hz, 1H), 6.93 (d, J=7.2 Hz, 1H), 6.88 (d, J=7.2 Hz, 1H), 4.90 (dd, J=9.0, 4.8 Hz, 1H), 4.27 (s, 2H), 4.00 (t, J=9.0 Hz, 1H), 3.63 (dd, J=9.0, 4.8 Hz, 1H), 3.29 (s, 3H).

Example 4(31)

2-[4-ethoxy-2-[4-methyl-2-(1-naphthyl)pentanoylamino]phenylmethyl]benzoic acid

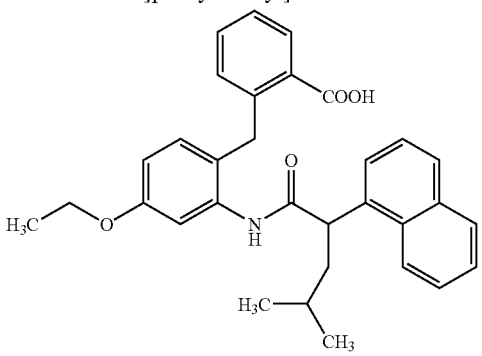

TLC: Rf 0.58 (chloroform:methanol=10:1); NMR (DMSO-d$_6$): δ 9.59 (s, 1H), 8.34 (d, J=8.4 Hz, 1H), 7.96 (d, J=8.4 Hz, 1H), 7.83 (d, J=7.8 Hz, 1H), 7.76 (d, J=6.9 Hz, 1H), 7.69–7.43 (m, 4H), 7.33–7.21 (m, 2H), 7.12 (s, 1H), 6.90 (d, J=7.8 Hz, 1H), 6.84 (d, J=7.2 Hz, 1H), 6.70 (d, J=8.4 Hz, 1H), 4.65 (m, 1H), 4.30 (d, J=16.5 Hz, 1H), 4.17 (d, J=16.5 Hz, 1H), 3.98 (q, J=6.9 Hz, 1H), 1.95 (m, 1H), 1.62–1.40 (m, 2H), 1.32 (t, J=6.9 Hz, 3H), 0.96 (d, J=6.0 Hz, 3H), 0.85 (d, J=6.0 Hz, 3H).

Example 4(32)

2-[4-isopropyloxy-2-[4-methyl-2-(1-naphthyl)pentanoylamino]phenylmethyl]benzoic acid

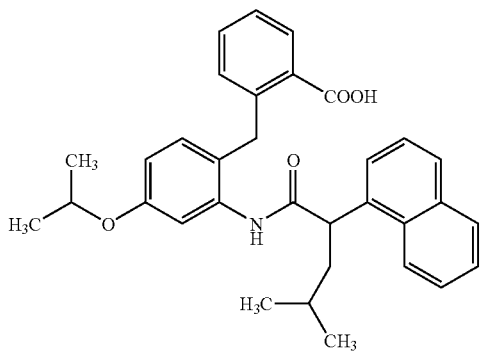

TLC: Rf 0.59 (chloroform:methanol=10:1); NMR (CDCl$_3$): δ 8.03 (d, J=7.2 Hz, 1H), 7.86–7.75 (m, 2H), 7.70–7.59 (m, 3H), 7.50–7.39 (m, 2H), 7.30–7.08 (m, 4H), 6.92 (d, J=8.4 Hz, 1H), 6.80 (d, J=7.8 Hz, 1H), 6.58 (dd, J=8.4, 2.4 Hz, 1H), 4.56 (m, 1H), 4.32 (t, J=7.2 Hz, 1H), 4.01 (d, J=16.8 Hz, 1H), 3.78 (d, J=16.8 Hz, 1H), 2.14 (m, 1H), 1.73 (m, 1H), 1.59 (m, 1H), 1.32 (d, J=6.3 Hz, 6H), 0.94 (d, J=6.6 Hz, 3H), 0.88 (d, J=6.6 Hz, 3H).

Example 4(33)

5-[2-[1,4-methyl-2-(1-naphthyl)pentanoylamino]phenylmethyl]oxazol-4-carboxylic acid

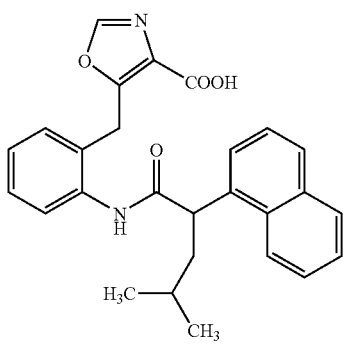

TLC: Rf 0.40 (chloroform:methanol=9:1); NMR (CDCl$_3$): δ 8.31 (d, J=8.4 Hz, 1H), 8.08 (s, 1H), 7.89–7.65 (m, 4H), 7.60–7.40 (m, 4H), 7.28–7.18 (m, 2H), 7.05 (t, J=7.2 Hz, 1H), 4.62 (t, J=7.8 Hz, 1H), 4.03 (d, J=16 Hz, 1H), 3.92 (d, J=16 Hz, 1H), 2.36 (m, 1H), 1.92 (m, 1H), 1.69 (m, 1H), 1.03 (d, J=6.6 Hz, 3H), 0.98 (d, J=6.6 Hz, 3H).

Example 4(34)

2-[4-methoxy-2-[4-methyl-2-(1-naphthyl)pentanoylamino]phenylmethyl]benzoic acid

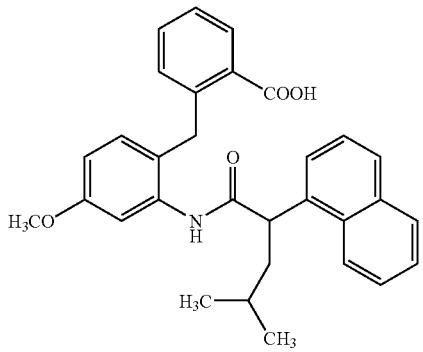

TLC: Rf 0.48 (chloroform:methanol=10:1); NMR (CDCl$_3$): δ 8.04 (d, J=7.8 Hz, 1H), 7.87 (d, J=2.7 Hz, 1H), 7.83–7.72 (m, 2H), 7.69–7.56 (m, 2H), 7.46 (m, 2H), 7.30–7.17 (m, 3H), 7.11 (m, 1H), 6.94 (d, J=8.7 Hz, 1H), 6.80 (d, J=7.8 Hz, 1H), 6.60 (dd, J=8.4, 2.4 Hz, 1H), 4.34 (t, J=7.2 Hz, 1H), 4.03 (d, J=16.8 Hz, 1H), 3.81(s, 3H), 3.79 (d, J=16.8 Hz, 1H), 2.14 (m, 1H), 1.72 (m, 1H), 1.60 (m, 1H), 0.95 (d, J=6.3 Hz, 3H), 0.88 (d, J=6.3 Hz, 3H)

EXAMPLE 5

2-[2-[2-[4-[2-(pyridin-2-yl)ethoxy]phenyl]propanoylamino]phenylmethyl]benzoic acid

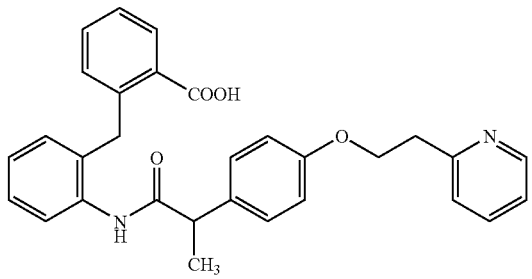

TLC: Rf 0.45 (chloroform:methanol=9:1); NMR (CDCl$_3$): δ 8.67 (d, J=4.5 Hz, 1H), 8.26 (dd, J=6.0, 3.3 Hz, 1H), 8.20 (d, J=8.1 Hz, 1H), 7.81 (dt, J=1.5 Hz, 1H), 7.40–7.28 (m, 5H), 7.10–7.07 (m, 2H), 6.86–6.77 (m, 5H), 6.67 (dd, J=5.4, 3.6 Hz, 1H), 4.48 (t, J=6.9 Hz, 2H), 4.04 (s, 2H), 3.52–3.40 (m, 3H), 1.39 (d, J=7.2 Hz, 3H).

Example 5(1)

2-[2-[2-[4-[2-(pyridin-4-yl)ethoxy]phenyl]propanoylamino]phenylmethyl]benzoic acid

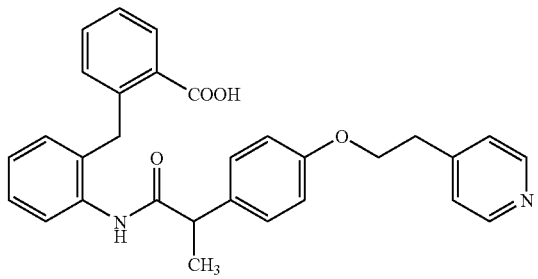

TLC: Rf 0.35 (chloroform:methanol=9:1); NMR (200 MHz, CDCl$_3$): δ 8.70 (s, 1H), 8.57 (br s, 1H), 8.11 (d, J=8.0

Hz, 1H), 7.99 (dd, J=6.1 Hz, 1H), 7.41–7.01 (m, 11H), 6.68 (d, J=8.8 Hz, 2H), 4.46 (d, J=16.1 Hz, 1H), 4.20 (t, J=6.2 Hz, 2H), 4.11 (d, J=16.1 Hz, 1H), 3.62 (q, J=7.0 Hz, 1H), 3.08 (t, J=6.2 Hz, 2H), 1.34 (d, J=7.0 Hz, 3H).

Example 5(2)

2-[4-cyano-2-(4-methyl-2-phenylpentanoylamino)phenylmethyl]benzoic acid

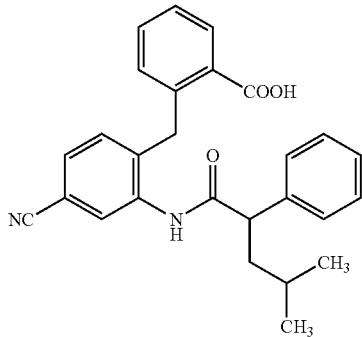

TLC: Rf 0.34 (chloroform:methanol=9:1); NMR (CDCl$_3$): δ 8.47 (s, 1H), 8.20 (s, 1H), 7.97 (brd, J=6.9 Hz, 1H), 7.43 (dt, J=7.8 Hz, 1.8 Hz, 1H), 7.36–7.14 (m, 8H), 7.03 (d, J=7.8 Hz, 1H), 4.21 (s, 2H), 3.57 (t, J=7.8 Hz, 1H), 2.10–1.30 (m, 3H), 0.86 (d, J=6.6 Hz, 3H), 0.85 (d, J=6.6 Hz, 3H).

Example 5(3)

2-[2-[2-(4-pentylphenyl)propanoylamino]phenylmethyl]benzoic acid

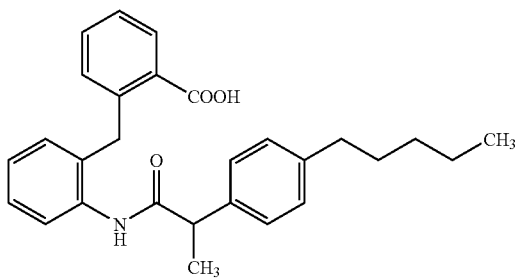

TLC: Rf 0.39 (chloroform:methanol=19:1); NMR (CDCl$_3$): δ 8.01 (d, J=7.8 Hz, 1H), 7.96 (d, J=7.8 Hz, 1H), 7.50 (bs, 1H), 7.44–7.20 (m, 3H), 7.11–6.93 (m, 7H), 4.16 (d, J=17 Hz, 1H), 4.12 (d, J=17 Hz, 1H), 3.61 (q, J=7.2 Hz, 1H), 2.51 (m, 2H), 1.47 (d, J=7.2 Hz, 3H), 1.62–1.19 (m, 6H), 0.86 (t, J=6.9 Hz, 3H).

FORMULATION EXAMPLE

Formulation Example 1

The following components were admixed by conventional techniques and punched out to give 100 tablets each containing 5 mg of active ingredient.

| | |
|---|---|
| 2-[2-[2-(1-naphthyl) propanoylamino] phenylmethyl] benzoic acid | 500 mg |
| calcium carboxymethylcellulose | 200 mg |
| magnesium stearate | 100 mg |
| microcrystalline cellulose | 9.2 g |

What is claimed is:

1. A benzoic acid derivative of formula (I)

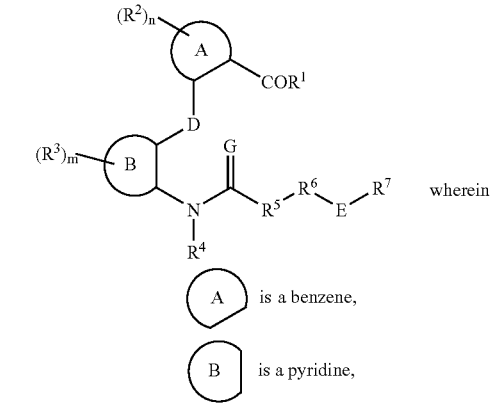 wherein

A is a benzene,

B is a pyridine,

D is methylene,
G is oxygen or sulfur,
E is a bond,
R$^1$ is hydroxy,
R$^4$ is hydrogen or C1–6 alkyl,
R$^5$ is branched C1–6 alkylene,
R$^6$ is naphthyl, and
R$^7$ is hydrogen,
or a non-toxic salt thereof.

2. The benzoic acid derivative according to claim 1, which is selected from
   (1) 2-[4-[2-(1-naphthyl)propanoylamino]pyridin-3-ylmethyl]benzoic acid,
   (2) 2-[3-[2-(1-naphthyl)propanoylamino]pyridin-2-yl methyl]benzoic acid, and
   (3) 2-[3-[2-(1-naphthyl)propanoylamino]pyridin-4-yl methyl]benzoic acid,
   or a methyl ester thereof or a non-toxic salt thereof.

3. A pharmaceutical composition comprising the benzoic acid derivative of formula (I) described in claim 1 or a non-toxic salt thereof as active ingredient.

* * * * *